(12) United States Patent
Friedman et al.

(10) Patent No.: US 10,342,697 B2
(45) Date of Patent: Jul. 9, 2019

(54) SYSTEMS AND METHODS FOR DELIVERING DRUGS TO AN EYE

(71) Applicant: Avedro, Inc., Waltham, MA (US)

(72) Inventors: Marc D. Friedman, Needham, MA (US); Pavel Kamaev, Lexington, MA (US); Stephen Zolla, Bedford, MA (US); Alexandra Nicklin, Cambridge, MA (US)

(73) Assignee: Avedro, Inc., Waltham, MA (US)

( * ) Notice: Subject to any disclaimer, the term of this patent is extended or adjusted under 35 U.S.C. 154(b) by 0 days.

(21) Appl. No.: 15/486,778

(22) Filed: Apr. 13, 2017

(65) Prior Publication Data

US 2017/0296383 A1 Oct. 19, 2017

Related U.S. Application Data

(60) Provisional application No. 62/321,830, filed on Apr. 3, 2016.

(51) Int. Cl.
*A61F 9/00* (2006.01)
*A61K 31/525* (2006.01)
*A61N 5/06* (2006.01)

(52) U.S. Cl.
CPC .......... *A61F 9/0008* (2013.01); *A61F 9/0017* (2013.01); *A61K 31/525* (2013.01); *A61N 5/062* (2013.01)

(58) Field of Classification Search
CPC ............................... A61F 9/008; A61F 9/0017
See application file for complete search history.

(56) References Cited

U.S. PATENT DOCUMENTS 4,838,851 A * 6/1989 Shabo .................... A45D 40/28
                                                    132/320
5,304,169 A    4/1994 Sand
(Continued)

FOREIGN PATENT DOCUMENTS

WO    2001/01959 A1    1/2001
WO    2005/049071 A2    6/2005
(Continued)

OTHER PUBLICATIONS

The International Search Report (ISR) with Written Opinion for PCT/US2017/027386 dated Aug. 3, 2017, pp. 1-7.

*Primary Examiner* — Edelmira Bosques
(74) *Attorney, Agent, or Firm* — McDonnell Boehnen Hulbert & Berghoff LLP

(57) ABSTRACT

A drug delivery device includes a drug-eluting element defined by a plurality of outer surfaces including a delivery surface and one or more other non-delivery surfaces. The delivery surface is positioned against tissue of an eye and shaped to define an area of targeted tissue to receive a drug. The drug-eluting element holds the drug when the delivery surface is not positioned against the tissue. Responsive to the delivery surface being positioned against the tissue, the drug-eluting element releases the drug to the area of targeted tissue through the delivery surface. The drug delivery device includes one or more barrier structures disposed along the one or more non-delivery surfaces of the drug-eluting element. The one or more barrier structures substantially inhibit release of the drug from the drug-eluting element through the one or more non-delivery surfaces.

15 Claims, 12 Drawing Sheets

(56) References Cited

U.S. PATENT DOCUMENTS

| | | |
|---|---|---|
| 5,484,432 A | 1/1996 | Sand |
| 5,519,931 A | 5/1996 | Reich |
| 5,618,284 A | 4/1997 | Sand |
| 6,161,544 A | 12/2000 | DeVore et al. |
| 6,537,545 B1 | 3/2003 | Karageozian et al. |
| 7,985,208 B2 | 7/2011 | Christensen |
| 8,466,203 B2 | 6/2013 | Paik et al. |
| 8,574,277 B2 | 11/2013 | Muller et al. |
| 8,834,916 B2 | 9/2014 | Newman |
| 8,945,101 B2 | 2/2015 | Herekar et al. |
| 9,044,308 B2 | 6/2015 | Muller et al. |
| 9,125,856 B1 | 9/2015 | Paik et al. |
| 9,155,652 B2 | 10/2015 | Peyman |
| 9,370,446 B2 | 6/2016 | Peyman |
| 9,399,102 B2 | 7/2016 | Dewoolfson et al. |
| 9,439,908 B2 | 9/2016 | Foschini et al. |
| 9,452,172 B2 | 9/2016 | Scherz et al. |
| 9,498,114 B2 | 11/2016 | Friedman et al. |
| 9,498,122 B2 | 11/2016 | Friedman et al. |
| 9,555,111 B2 | 1/2017 | Rubinfeld et al. |
| 9,707,126 B2 | 7/2017 | Friedman et al. |
| 2001/0016731 A1 | 8/2001 | DeVore et al. |
| 2003/0175259 A1 | 9/2003 | Karageozian et al. |
| 2006/0276777 A1 | 12/2006 | Coroneo |
| 2007/0088415 A1 | 4/2007 | Peyman |
| 2007/0135805 A1 | 6/2007 | Peyman |
| 2007/0142828 A1 | 6/2007 | Peyman |
| 2009/0105127 A1 | 4/2009 | Thompson et al. |
| 2009/0192437 A1 | 7/2009 | Soltz et al. |
| 2010/0057060 A1 | 3/2010 | Herekar |
| 2010/0082018 A1 | 4/2010 | Panthakey et al. |
| 2010/0286156 A1 | 11/2010 | Pinelli |
| 2011/0060267 A1 | 3/2011 | DeWoolfson et al. |
| 2011/0086802 A1 | 4/2011 | DeWoolfson et al. |
| 2011/0098790 A1 | 4/2011 | Daxer |
| 2011/0152219 A1 | 6/2011 | Stagni et al. |
| 2011/0237999 A1 | 9/2011 | Muller et al. |
| 2011/0288466 A1 | 11/2011 | Muller et al. |
| 2012/0065572 A1 | 3/2012 | Lewis et al. |
| 2012/0078362 A1 | 3/2012 | Haffner et al. |
| 2012/0203161 A1 | 8/2012 | Herekar |
| 2012/0215155 A1 | 8/2012 | Muller et al. |
| 2012/0238938 A1 | 9/2012 | Herekar et al. |
| 2012/0283621 A1 | 11/2012 | Muller |
| 2012/0289886 A1 | 11/2012 | Muller et al. |
| 2012/0310083 A1 | 12/2012 | Friedman et al. |
| 2013/0058954 A1 | 3/2013 | Sutton et al. |
| 2013/0085370 A1 | 4/2013 | Friedman et al. |
| 2013/0178821 A1 | 7/2013 | Foschini et al. |
| 2013/0245536 A1 | 9/2013 | Friedman et al. |
| 2013/0310728 A1 | 11/2013 | Seiler et al. |
| 2013/0310732 A1 | 11/2013 | Foschini et al. |
| 2014/0022507 A1 | 1/2014 | Nicolson et al. |
| 2014/0066835 A1 | 3/2014 | Muller et al. |
| 2014/0113009 A1 | 4/2014 | Muller et al. |
| 2014/0171926 A1 | 6/2014 | Depfenhart |
| 2014/0171927 A1 | 6/2014 | Depfenhart |
| 2014/0249509 A1 | 9/2014 | Rubinfeld et al. |
| 2014/0276361 A1 | 9/2014 | Herekar et al. |
| 2014/0277431 A1 | 9/2014 | Herekar et al. |
| 2014/0320819 A1 | 10/2014 | Muller et al. |
| 2014/0343480 A1 | 11/2014 | Kamaev et al. |
| 2014/0379054 A1 | 12/2014 | Cooper et al. |
| 2015/0164791 A1 | 6/2015 | Coroneo |
| 2015/0209181 A1 | 7/2015 | Herekar et al. |
| 2015/0320595 A1 | 11/2015 | Blumenkranz et al. |
| 2015/0342784 A1 | 12/2015 | Seiler et al. |
| 2015/0374540 A1 | 12/2015 | Lopath et al. |
| 2016/0000885 A1 | 1/2016 | Thompson et al. |
| 2016/0022493 A1 | 1/2016 | Peyman |
| 2016/0059032 A1 | 3/2016 | Skerl |
| 2016/0135989 A1 | 5/2016 | Wellhoefer |
| 2016/0143777 A1 | 5/2016 | Roy et al. |
| 2016/0175147 A1 | 6/2016 | Lopath |
| 2016/0175442 A1 | 6/2016 | Kamaev et al. |
| 2016/0236006 A1 | 8/2016 | Donitzky et al. |
| 2016/0310319 A1 | 10/2016 | Friedman et al. |
| 2016/0310758 A1 | 10/2016 | Friedman et al. |
| 2016/0338588 A1 | 11/2016 | Friedman |
| 2017/0007395 A1 | 1/2017 | Peyman |
| 2017/0021021 A1 | 1/2017 | Kamaev et al. |
| 2017/0043015 A1 | 2/2017 | Alageel et al. |
| 2017/0156926 A1 | 6/2017 | Friedman et al. |

FOREIGN PATENT DOCUMENTS

| | | |
|---|---|---|
| WO | 2009/001396 A1 | 12/2008 |
| WO | 2009/120550 A2 | 10/2009 |

* cited by examiner ically inhibit release of the drug from the drug-eluting element through the one or more non-delivery surfaces. In further embodiments, one or more of the barrier structures are disposed around a periphery of the delivery surface and are configured to substantially inhibit flow of the drug beyond the periphery of the delivery surface.

SYSTEMS AND METHODS FOR DELIVERING DRUGS TO AN EYE

CROSS REFERENCE TO RELATED APPLICATIONS

This application claims priority to U.S. Provisional Patent Application No. 62/321,830, filed Apr. 13, 2016, the contents of which are incorporated entirely herein by reference.

FIELD OF THE INVENTION

The present disclosure pertains to systems and methods for treating disorders of the eye, and more particularly, to systems and methods for delivering drugs to different eye tissues for such treatments.

SUMMARY

An example drug delivery device includes a drug-eluting element and one or more barrier structures. The drug-eluting element is configured to receive a drug (e.g., one or more chemical substances) for treating a disorder of the eye. When applied, the drug delivery device positions the drug-eluting element at or near tissue targeted for treatment. The targeted tissue can absorb the drug from the drug-eluting element. The barrier structures help to prevent the release of the drug to other parts of the eye, i.e., non-targeted tissue. As such, the drug delivery device provides focal delivery of the drug to tissue specifically targeted for treatment.

In an example implementation, the drug delivery device may be employed to apply a cross-linking agent, e.g., riboflavin formulation, to a selected portion of corneal tissue or other ocular tissues. Correspondingly, the drug delivery device may be employed in combination with a light delivery system to photoactivate the cross-linking agent and generate cross-linking activity in the portion of corneal tissue.

In another example implementation, the drug delivery device may be employed to apply antimicrobial, antibiotic, and/or other therapeutic agents to selected portions of ocular tissue such as the cornea, sclera, eyelid, etc.

According to an example embodiment, a drug delivery device includes a drug-eluting element defined by a plurality of outer surfaces. The outer surfaces include a delivery surface and one or more other non-delivery surfaces. The delivery surface is configured to be positioned against tissue of an eye and shaped to define an area of targeted tissue to receive a drug. The drug-eluting element is configured to hold the drug when the delivery surface is not positioned against the tissue. Responsive to the delivery surface being positioned against the tissue, the drug-eluting element is configured to release the drug to the area of targeted tissue through the delivery surface. The drug delivery device includes one or more barrier structures disposed along the one or more non-delivery surfaces of the drug-eluting element. The one or more barrier structures are configured to substantially inhibit release of the drug from the drug-eluting element through the one or more non-delivery surfaces. In further embodiments, one or more of the barrier structures are disposed around a periphery of the delivery surface and are configured to substantially inhibit flow of the drug beyond the periphery of the delivery surface.

According to another example embodiment, a method for drug delivery includes providing a drug delivery device. The drug delivery device includes a drug-eluting element defined by a plurality of outer surfaces. The outer surfaces include a delivery surface and one or more other non-delivery surfaces. The drug delivery device includes one or more barrier structures disposed along the one or more non-delivery surfaces of the drug-eluting element. The method includes loading the drug-eluting element with a drug. The method includes positioning the delivery surface of the drug-eluting element against tissue of an eye. The method includes releasing the drug from the drug-eluting element via the delivery surface to an area of targeted tissue determined by a shape of the delivery surface. The one or more barrier structures of the drug delivery device are configured to substantially inhibit release of the drug from the drug-eluting element through the one or more non-delivery surfaces. In further embodiments, one or more of the barrier structures are disposed around a periphery of the delivery surface and are configured to substantially inhibit flow of the drug beyond the periphery of the delivery surface.

DESCRIPTION

Cross-linking treatments may be employed to treat eyes suffering from disorders, such as keratoconus. In particular, keratoconus is a degenerative disorder of the eye in which structural changes within the cornea cause it to weaken and change to an abnormal conical shape. Cross-linking treatments can strengthen and stabilize areas weakened by keratoconus and prevent undesired shape changes.

Cross-linking treatments may also be employed after surgical procedures, such as Laser-Assisted in situ Keratomileusis (LASIK) surgery. For instance, a complication known as post-LASIK ectasia may occur due to the thinning and weakening of the cornea caused by LASIK surgery. In post-LASIK ectasia, the cornea experiences progressive steepening (bulging). Accordingly, cross-linking treatments can strengthen and stabilize the structure of the cornea after LASIK surgery and prevent post-LASIK ectasia.

Cross-linking treatments may be employed to treat eyes suffering from refractive disorders, such as myopia, hyperopia and or astigmatism. In particular, myopia is a disorder of the eye in which structural aspects of the eye cause light to focus short of the retina causing blurred vision. Cross-linking treatments can flatten areas of the cornea and producing a desired shape change reducing or eliminating myopia.

Figure 1:
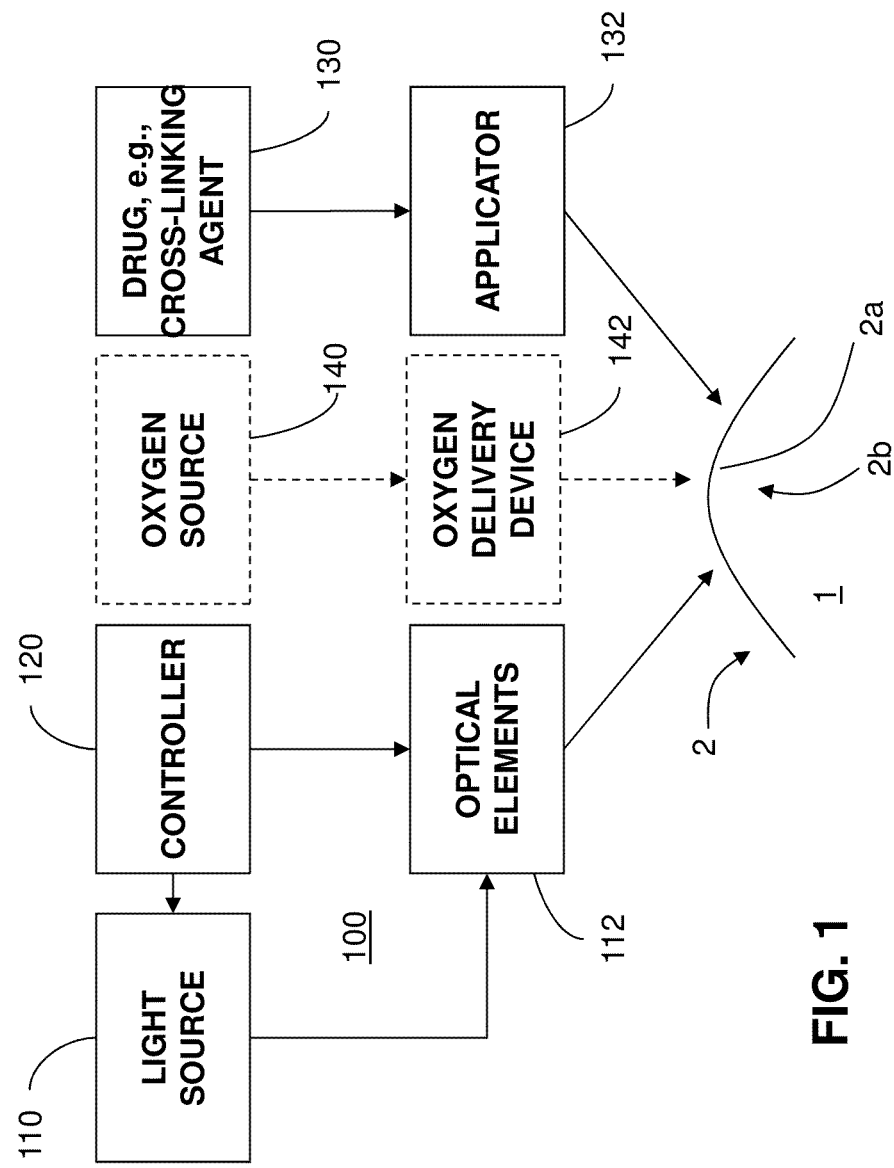
FIG. 1 illustrates an example system that delivers a cross-linking agent and photoactivating light to a cornea of an eye in order to generate cross-linking of corneal collagen.

FIG. 1 illustrates an example treatment system 100 for generating cross-linking of collagen in a cornea 2 of an eye 1. The treatment system 100 includes an applicator 132 for applying a cross-linking agent 130 to the cornea 2. In example embodiments, the applicator 132 may be an eye dropper, syringe, or the like that applies the photosensitizer 130 as drops to the cornea 2. The cross-linking agent 130 may be provided in a formulation that allows the cross-linking agent 130 to pass through the corneal epithelium 2a and to underlying regions in the corneal stroma 2b. Alternatively, the corneal epithelium 2a may be removed or otherwise incised to allow the cross-linking agent 130 to be applied more directly to the underlying tissue.

The treatment system 100 includes a light source 110 and optical elements 112 for directing light to the cornea 2. The light causes photoactivation of the cross-linking agent 130 to generate cross-linking activity in the cornea 2. For example, the cross-linking agent may include riboflavin and the photoactivating light may be ultraviolet A (UVA) (e.g., 365 nm) light. Alternatively, the photoactivating light may have another wavelength, such as a visible wavelength (e.g., 452 nm). As described further below, corneal cross-linking improves corneal strength by creating chemical bonds within the corneal tissue according to a system of photochemical kinetic reactions. For instance, riboflavin and the photoactivating light are applied to stabilize and/or strengthen corneal tissue to address diseases such as keratoconus or post-LASIK ectasia.

The treatment system 100 includes one or more controllers 120 that control aspects of the system 100, including the light source 110 and/or the optical elements 112. In an implementation, the cornea 2 can be more broadly treated with the cross-linking agent 130 (e.g., with an eye dropper, syringe, etc.), and the photoactivating light from the light source 110 can be selectively directed to regions of the treated cornea 2 according to a particular pattern.

The optical elements 112 may include one or more mirrors or lenses for directing and focusing the photoactivating light emitted by the light source 110 to a particular pattern on the cornea 2. The optical elements 112 may further include filters for partially blocking wavelengths of light emitted by the light source 110 and for selecting particular wavelengths of light to be directed to the cornea 2 for activating the cross-linking agent 130. In addition, the optical elements 112 may include one or more beam splitters for dividing a beam of light emitted by the light source 110, and may include one or more heat sinks for absorbing light emitted by the light source 110. The optical elements 112 may also accurately and precisely focus the photo-activating light to particular focal planes within the cornea 2, e.g., at a particular depths in the underlying region 2b where cross-linking activity is desired.

Moreover, specific regimes of the photoactivating light can be modulated to achieve a desired degree of cross-linking in the selected regions of the cornea 2. The one or more controllers 120 may be used to control the operation of the light source 110 and/or the optical elements 112 to precisely deliver the photoactivating light according to any combination of: wavelength, bandwidth, intensity, power, location, depth of penetration, and/or duration of treatment (the duration of the exposure cycle, the dark cycle, and the ratio of the exposure cycle to the dark cycle duration).

The parameters for photoactivation of the cross-linking agent 130 can be adjusted, for example, to reduce the amount of time required to achieve the desired cross-linking. In an example implementation, the time can be reduced from minutes to seconds. While some configurations may apply the photoactivating light at an irradiance of 5 mW/cm$^2$, larger irradiance of the photoactivating light, e.g., multiples of 5 mW/cm$^2$, can be applied to reduce the time required to achieve the desired cross-linking. The total dose of energy absorbed in the cornea 2 can be described as an effective dose, which is an amount of energy absorbed through an area of the corneal epithelium 2a. For example the effective dose for a region of the corneal surface 2A can be, for example, 5 J/cm$^2$, or as high as 20 J/cm$^2$ or 30 J/cm$^2$. The effective dose described can be delivered from a single application of energy, or from repeated applications of energy.

The optical elements 112 of the treatment system 100 may include a digital micro-mirror device (DMD) to modulate the application of photoactivating light spatially and temporally. Using DMD technology, the photoactivating light from the light source 110 is projected in a precise spatial pattern that is created by microscopically small mirrors laid out in a matrix on a semiconductor chip. Each mirror represents one or more pixels in the pattern of projected light. With the DMD one can perform topography guided cross-linking. The control of the DMD according to topography may employ several different spatial and temporal irradiance and dose profiles. These spatial and temporal dose profiles may be created using continuous wave illumination but may also be modulated via pulsed illumination by pulsing the illumination source under varying frequency and duty cycle regimes as described above. Alternatively, the DMD can modulate different frequencies and duty cycles on a pixel by pixel basis to give ultimate flexibility using continuous wave illumination. Or alternatively, both pulsed illumination and modulated DMD frequency and duty cycle combinations may be combined. This allows for specific amounts of spatially determined corneal cross-linking. This spatially determined cross-linking may be combined with dosimetry, interferometry, optical coherence tomography (OCT), corneal topography, etc., for pre-treatment planning and/or real-time monitoring and modulation of corneal cross-linking during treatment. Additionally, pre-clinical patient information may be combined with finite element biomechanical computer modeling to create patient specific pre-treatment plans.

To control aspects of the delivery of the photoactivating light, embodiments may also employ aspects of multiphoton excitation microscopy. In particular, rather than delivering a single photon of a particular wavelength to the cornea 2, the treatment system 100 may deliver multiple photons of longer wavelengths, i.e., lower energy, that combine to initiate the cross-linking. Advantageously, longer wavelengths are scattered within the cornea 2 to a lesser degree than shorter wavelengths, which allows longer wavelengths of light to penetrate the cornea 2 more efficiently than shorter wavelength light. Shielding effects of incident irradiation at deeper depths within the cornea are also reduced over conventional short wavelength illumination since the absorption of the light by the photosensitizer is much less at the longer wavelengths. This allows for enhanced control over depth specific cross-linking. For example, in some embodiments, two photons may be employed, where each photon carries approximately half the energy necessary to excite the molecules in the cross-linking agent 130 to generate the photochemical kinetic reactions described further below. When a cross-linking agent molecule simultaneously absorbs both photons, it absorbs enough energy to release reactive radicals in the corneal tissue. Embodiments may also utilize lower energy photons such that a cross-linking agent molecule must simultaneously absorb, for example, three, four, or five, photons to release a reactive radical. The probability of the near-simultaneous absorption of multiple photons is low, so a high flux of excitation photons may be required, and the high flux may be delivered through a femtosecond laser.

A large number of conditions and parameters affect the cross-linking of corneal collagen with the cross-linking agent 130. For example, when the cross-linking agent 130 is riboflavin and the photoactivating light is UVA light, the irradiance and the dose both affect the amount and the rate of cross-linking. The UVA light may be applied continuously (continuous wave (CW)) or as pulsed light, and this selection has an effect on the amount, the rate, and the extent of cross-linking.

If the UVA light is applied as pulsed light, the duration of the exposure cycle, the dark cycle, and the ratio of the exposure cycle to the dark cycle duration have an effect on the resulting conical stiffening. Pulsed light illumination can be used to create greater or lesser stiffening of corneal tissue than may be achieved with continuous wave illumination for the same amount or dose of energy delivered. Light pulses of suitable length and frequency may be used to achieve more optimal chemical amplification. For pulsed light treatment, the on/off duty cycle may be between approximately 1000/1 to approximately 1/1000; the irradiance may be between approximately 1 mW/cm$^2$ to approximately 1000 mW/cm$^2$ average irradiance, and the pulse rate may be between approximately 0.01 HZ to approximately 1000 Hz or between approximately 1000 Hz to approximately 100,000 Hz.

The treatment system 100 may generate pulsed light by employing a DMD, electronically turning the light source 110 on and off, and/or using a mechanical or opto-electronic (e.g., Pockels cells) shutter or mechanical chopper or rotating aperture. Because of the pixel specific modulation capabilities of the DMD and the subsequent stiffness impartment based on the modulated frequency, duty cycle, irradiance and dose delivered to the cornea, complex biomechanical stiffness patterns may be imparted to the cornea to allow for various amounts of refractive correction. These refractive corrections, for example, may involve combinations of myopia, hyperopia, astigmatism, irregular astigmatism, presbyopia and complex corneal refractive surface corrections because of ophthalmic conditions such as keratoconus, pellucid marginal disease, post-lasik ectasia, and other conditions of corneal biomechanical alteration/degeneration, etc. A specific advantage of the DMD system and method is that it allows for randomized asynchronous pulsed topographic patterning, creating a non-periodic and uniformly appearing illumination which eliminates the possibility for triggering photosensitive epileptic seizures or flicker vertigo for pulsed frequencies between 2 Hz and 84 Hz.

Although example embodiments may employ stepwise on/off pulsed light functions, it is understood that other functions for applying light to the cornea may be employed to achieve similar effects. For example, light may be applied to the cornea according to a sinusoidal function, sawtooth function, or other complex functions or curves, or any combination of functions or curves. Indeed, it is understood that the function may be substantially stepwise where there may be more gradual transitions between on/off values. In addition, it is understood that irradiance does not have to decrease down to a value of zero during the off cycle, and may be above zero during the off cycle. Desired effects may be achieved by applying light to the cornea according to a curve varying irradiance between two or more values.

Examples of systems and methods for delivering photoactivating light are described, for example, in U.S. Patent Application Publication No. 2011/0237999, filed Mar. 18, 2011 and titled "Systems and Methods for Applying and Monitoring Eye Therapy," U.S. Patent Application Publication No. 2012/0215155, filed Apr. 3, 2012 and titled "Systems and Methods for Applying and Monitoring Eye Therapy," and U.S. Patent Application Publication No.

2013/0245536, filed Mar. 15, 2013 and titled "Systems and Methods for Corneal Cross-Linking with Pulsed Light," the contents of these applications being incorporated entirely herein by reference.

The addition of oxygen also affects the amount of corneal stiffening. In human tissue, $O_2$ content is very low compared to the atmosphere. The rate of cross-linking in the cornea, however, is related to the concentration of $O_2$ when it is irradiated with photoactivating light. Therefore, it may be advantageous to increase or decrease the concentration of $O_2$ actively during irradiation to control the rate of cross-linking until a desired amount of cross-linking is achieved. Oxygen may be applied during the cross-linking treatments in a number of different ways. One approach involves supersaturating the riboflavin with $O_2$. Thus, when the riboflavin is applied to the eye, a higher concentration of $O_2$ is delivered directly into the cornea with the riboflavin and affects the reactions involving $O_2$ when the riboflavin is exposed to the photoactivating light. According to another approach, a steady state of $O_2$ (at a selected concentration) may be maintained at the surface of the cornea to expose the cornea to a selected amount of $O_2$ and cause $O_2$ to enter the cornea. As shown in FIG. 1, for instance, the treatment system 100 also includes an oxygen source 140 and an oxygen delivery device 142 that optionally delivers oxygen at a selected concentration to the cornea 2. Example systems and methods for applying oxygen during cross-linking treatments are described, for example, in U.S. Pat. No. 8,574,277, filed Oct. 21, 2010 and titled "Eye Therapy," U.S. Patent Application Publication No. 2013/0060187, filed Oct. 31, 2012 and titled "Systems and Methods for Corneal Cross-Linking with Pulsed Light," the contents of these applications being incorporated entirely herein by reference.

Figure 2:
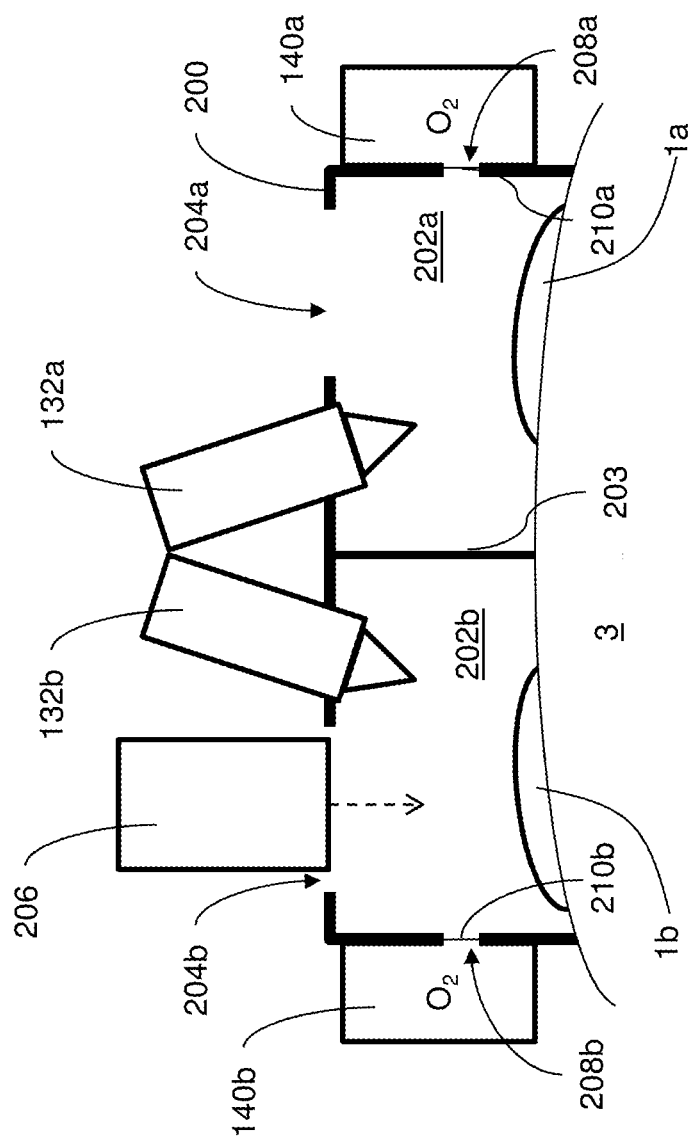
FIG. 2 illustrates an example device for applying cross-linking treatments, according to aspects of the present disclosure.

FIG. 2 illustrates an example treatment device 200 for applying cross-linking treatment to both eyes 1a, b of a patient. Aspects of the treatment system 100 described above may be incorporated into the treatment device 200. As shown in FIG. 2, the treatment device 200 is configured to be positioned on the patient's face 3 and to fit over both the right eye 1a and the left eye 1b. The treatment device 200 may be kept in position on the patient's face 3 by a strap (not shown) that can be worn around the patient's head. As such, in some aspects, the treatment device 200 may resemble a pair of goggles or a mask. Alternatively, medical tape or the like may be applied to the treatment device 200 and the face 3 to keep the treatment device 200 in position. Alternatively, the treatment device 200 may rest stably on the patient's face 3 without additional support while the patient is lying on his/her back. In some cases, a speculum may be applied to each eye 1a, b to keep the eyelids from closing during the treatment. In such cases, the treatment device 200 may be configured to fit around or otherwise accommodate the use of the specula. The treatment device 200 may be employed for cross-linking treatments with an intact corneal epithelium (epi-on) or without an intact corneal epithelium (epi-off).

The treatment device 200 includes a right section 202a that is positioned over the right eye 1a and a left section 202b that is positioned over the left eye 1b. Each section 202a, b is configured to provide cross-linking treatment for the cornea in the respective eye 1a, b. The sections 202a, b may be physically divided by a wall 203 as shown in FIG. 2 to reduce any likelihood that treatment of one eye will affect treatment of the other eye. The wall 203, however, may be omitted in alternative embodiments.

Each section 202a, b includes a cross-linking applicator 132a, b, as described above. As shown in FIG. 2, the applicators 132a, b are integrated into the treatment device 200. Each applicator 132a, b can apply a cross-linking agent solution, such as a riboflavin formulation, to the cornea of each eye 1a, b, respectively. For instance, each delivery device 132a, b may include aspects of an eye dropper, syringe, or the like from which the cross-linking agent solution can be dripped onto the cornea.

In addition to employing the applicators 132a, b to deliver an initial dose of cross-linking agent to the eyes 1a, b, the applicators 132a, b or other similar applicators can be further employed to irrigate the eyes 1a, b periodically to keep them moist during treatment. For instance, the eyes 1a, b may be irrigated with saline or additional cross-linking agent solution. Additionally, the applicators 132a, b or other similar applicators may apply solutions containing other agents. For instance, such agents may enhance the amount of cross-linking activity, particularly with epi-on treatments. Other agents may quench the cross-linking activity generated by the cross-linking agent. Yet other agents may include an antibiotic to provide antimicrobial treatment.

Each section 202a, b may also include an opening 204a, b that is positioned over each eye 1a, b, respectively. An illumination device 206 may be positioned relative to the treatment device 200 to deliver a dose of photoactivating light through one of the openings 204,a, b to the respective eye 1a, b. If the cross-linking agent is riboflavin, the photoactivating light may be ultraviolet light. The illumination device 206 may include the light source 110 and the optical elements 112 as described above.

As shown in FIG. 2, the illumination device 206 is positioned over the opening 204b and can deliver the photoactivating light to the cornea of the left eye 1b after the cross-linking agent has been applied to the cornea. In some cases, the illumination device 206 is separately supported, e.g., by a stand, over the opening 204a, b. In other cases, the illumination device 206 may be fixedly coupled to the treatment device 200.

The dose, irradiation, pattern, pulsing/continuous wave, and other treatment parameters for the photoactivating light may be controlled as described above. For instance, the controller 120 may be coupled to the light source 110 and/or the optical elements 112. Accordingly, the photoactivating light from the illumination device 206 generates cross-linking activity in the cornea.

As shown in FIG. 2, the applicators 132a, b are integrated into the treatment device 200 for delivering the cross-linking agent to the eyes 1a, b. In alternative embodiments, however, a separate cross-linking applicator 132 may be introduced through the openings 204a, b to apply the cross-linking agent to the corneas of the eyes 1a, b.

Each section 202a, b may also allow a concentration of oxygen gas to be delivered from an oxygen source 140 to the eyes 1a, b. As described above, the oxygen gas enhances or otherwise controls the cross-linking activity during photoactivation. As shown in FIG. 2, each section 202a, b may include a respective oxygen source 140a, b integrated into the treatment device 200. The oxygen from each oxygen source 140a, b can be released into the section 202a, b through an opening 208a, b, respectively. The treatment device 200 is configured so that the oxygen is introduced with minimal turbulence. The release can be controlled by removing a seal 210a, b that is placed over the opening 208a, b, respectively. For instances, the seal 210a, b may be a pull-off tab that can be manually removed by the practitioner. In alternative embodiments, rather than integrating the oxygen sources 140a, b into the treatment device 200, each section 202a, b may include a port that can be coupled to a controllable external oxygen source 140.

Where two illumination devices 206 are available, the treatment device 200 allows both eyes 1a, b to be treated with the photoactivating light simultaneously. As such, both eyes 1a, b can be treated with the same steps (cross-linking agent application, photo activation) simultaneously.

Where only one illumination device 206 is available, however, the eyes 1a, b can be alternately treated with the photoactivating light. For instance, FIG. 2 shows a single illumination device 206 that treats one eye 1a, b at a time. Advantageously, the treatment device 200 allows one eye to be treated with photoactivating light, while allowing the other eye to be treated with the cross-linking agent. As shown in FIG. 2, the right eye 1a can be soaked with the cross-linking agent from the applicator 132a, while the left eye 1b receives the photoactivating light after having already been soaked in the cross-linking agent from the applicator 132b. After the application of photoactivating light to the left eye 1b is complete, the illumination device 206 may be shifted to the opening 104a to deliver photoactivating light to the right eye 1a. By allowing both eyes 1a, b to receive some treatment step at the same time, the total treatment time can be reduced significantly even when only one illumination device 206 available. For instance, with the treatment device, the single illumination device 206 may be used to treat at least four pairs of eyes in one hour depending on treatment parameters.

In general, the structure of the cornea includes five layers. From the outer surface of the eye inward, these are: (1) epithelium, (2) Bowman's layer, (3) stroma, (4) Descemet's membrane, and (5) endothelium. During example cross-linking treatments, the stroma is treated with riboflavin, a photosensitizer, and ultraviolet (UV) light is delivered to the cornea to activate the riboflavin in the stroma. Upon absorbing UV radiation, riboflavin undergoes a reaction with oxygen in which reactive oxygen species and other radicals are produced. These reactive oxygen species and other radicals further interact with the collagen fibrils to induce covalent bonds that bind together amino acids of the collagen fibrils, thereby cross-linking the fibrils. The photo-oxidative induction of collagen cross-linking enhances the biomechanical strength of the stroma, and can provide therapeutic benefits for certain ophthalmic conditions, such as keratoconus, or generate refractive changes to correct myopia, hyperopia and/or astigmatism.

As the outer-most barrier of the cornea, the epithelium functions to regulate nutrients, including oxygen, that are admitted into the stromal tissue from the tear film. This regulation is carried out via the epithelium's physiological "pumps" that are driven by osmotic pressure across the epithelium due to differential concentrations of barrier-permeable solutes on either side of the epithelium. When healthy, certain nutrients in the tear film that become depleted within the stroma can permeate the epithelium via osmotic pressure to resupply the stroma. However, while oxygen and some other small molecule nutrients can reach the stroma according to this mechanism, certain photosensitizers cannot pass through the epithelium.

Riboflavin, for example, is a relatively large, hydrophilic molecule that cannot penetrate the tight junctions of the epithelium. The epithelium slows the amount of riboflavin that can penetrate the stroma. Thus, a variety of approaches have been employed to overcome low riboflavin diffusivity and deliver sufficient concentrations of riboflavin to the stroma for performing corneal cross-linking treatments. According to one approach, the epithelium is removed (epithelium debridement) before a riboflavin solution is applied directly to the stroma. Although removing the epithelium allows riboflavin to reach the stroma, the approach is associated with patient discomfort, risks of infection, and other possible complications.

Meanwhile, other approaches avoid epithelial debridement. For example, riboflavin may be provided in a formulation that allows the cross-linking agent to pass through the epithelium. Such formulations are described, for example, in U.S. Patent Application Publication No. 2010/0286156, filed on May 6, 2009 and titled "Collyrium for the Treatment of Conical Cornea with Cross-Linking Trans-Epithelial Technique, and in U.S. Patent Application Publication No. 2013/0267528, filed on Jan. 4, 2013 and titled "Trans-Epithelial Osmotic Collyrium for the Treatment of Keratoconus," the contents of these applications being incorporated entirely herein by reference. In particular, some riboflavin formulations include ionic agents, such as benzalkonium chloride (BAC), with a specific osmolarity of sodium chloride (NaCl). Although such formulations may enhance permeability of the epithelium, they are disadvantageously corrosive to the epithelium.

Additionally or alternatively, another solution and/or mechanical forces may be applied to enhance the permeability of the epithelium and allow the riboflavin to pass more easily through the epithelium. Examples of approaches for enhancing or otherwise controlling the delivery of a cross-linking agent to the underlying regions of the cornea are described, for example, in U.S. Patent Application Publication No. 2011/0288466, filed Apr. 13, 2011 and titled "Systems and Methods for Activating Cross-Linking in an Eye," and U.S. Patent Application Publication No. 2012/0289886, filed May 18, 2012 and titled "Controlled Application of Cross-Linking Agent," the contents of these applications being incorporated entirely herein by reference. The present disclosure teaches the use of another class of riboflavin formulations. Advantageously, such formulations enhance the permeability of the epithelium sufficiently to allow relatively large hydrophilic riboflavin molecules (or Flavin mononucleotide (FMN), or riboflavin-5'-phosphate, molecules) to pass through the epithelium without debridement, but the permeability is not enhanced to a point where the epithelium becomes damaged. To enhance permeability, such formulations employ a non-ionic agent that is chosen using the Hydrophile-Lipophile Balance (HLB) system.

The HLB of a permeability enhancer indicates the balance of hydrophilic and lipophilic groups in the molecular structure of the enhancer. Permeability enhancers (or emulsifiers) for the epithelium include a molecule which has both hydrophilic and lipophilic groups. Molecules with HLB number below 9 are considered lipophilic and those above 11 as hydrophilic. Molecules with HLB number between 9 and 11 are intermediate.

For the corneal epithelium, a HLB number that is too great or too small does not help the passage of a photosensitizer through the epithelium. A specific HLB range enhances movement of a photosensitizer through the epithelium. Thus, aspects of the present disclosure employ non-ionic agents that have a hydrophilic/lipophilic balance to achieve optimized diffusivity through the epithelium and the stroma. Advantageously, non-ionic agents are also less corrosive and damaging to the epithelium than ionic agents, such as BAC.

For riboflavin, the HLB range for more effective permeability enhancers has been experimentally determined by the inventors to be between approximately 12.6 and approximately 14.6. A class of permeability enhancers includes various forms of polyethylene glycol (PEG) with different aliphatic chain lengths. According to example embodiments, some riboflavin formulations include specific concentrations of Polidocanol (Polyoxyethylene (9) lauryl ether), which has a HLB number of approximately 13.6.

To calculate the HLB for molecules or combinations of molecules where the hydrophilic portion consists of ethylene oxide only, the formula is:

$$HLB = E/5, \text{ where } E = \text{weight percentage oxyethylene content.}$$

In general, the HLB range for enhancers that achieve more effective permeability may vary according to different aspects of the formulation. In particular, the HLB range for more optimal enhancers may vary according to the photosensitizer employed in the formulation. For instance, more optimal permeability might be achieved for other photosensitizers, such as Rose Bengal, by employing enhancers in a HLB range that is different from that for riboflavin (e.g., HLB of approximately 12.6 to approximately 14.6).

Furthermore, the formulation may include other additives that may affect the HLB range for more optimal enhancers. For instance, riboflavin formulations may also include iron ions, such as Fe(II). Additives that may be included in photosensitizer formulations are described, for example, in U.S. Patent Application Publication No. 2014/0343480, filed May 19, 2014 and titled "Systems, Methods, and Compositions for Cross-linking," and U.S. Provisional Patent Application No. 62/086,572, filed Dec. 2, 2014 and titled "Systems, Methods, and Compositions for Cross-linking," the contents of these applications being incorporated entirely herein by reference.

Additionally, several permeability enhancers may be combined to achieve a specific HLB that achieves more effective permeability for the epithelium. These may be calculated by taking the percentage of each enhancer, multiplying it by its HLB number, and then summing the results. For instance, in a formulation including 30% enhancer A with a HLB number of approximately 14, 50% enhancer B with a HLB number of approximately 6, and 20% enhancer C with a HLB number of approximately 14, the estimated HLB number can be calculated as:

$$30\% \times HLB14 \text{ for } A = 4.2;$$

$$50\% \times HLB6 \text{ for } B = 3.0;$$

$$20\% \times HLB14 \text{ for } C = 2.8;$$

$$\text{Estimated HLB number for combination of } A+B+C = 4.2+3.0+2.8 = 10.0$$

Thus, two or more enhancers may be combined to achieve a very specific HLB number, where a single enhancer may provide less optimal permeability. Additionally, combining different enhancers might offer other desirable properties of the final formulation with regard to solubility, viscosity, stability or some other desirable attribute.

Study 1

Figure 3:
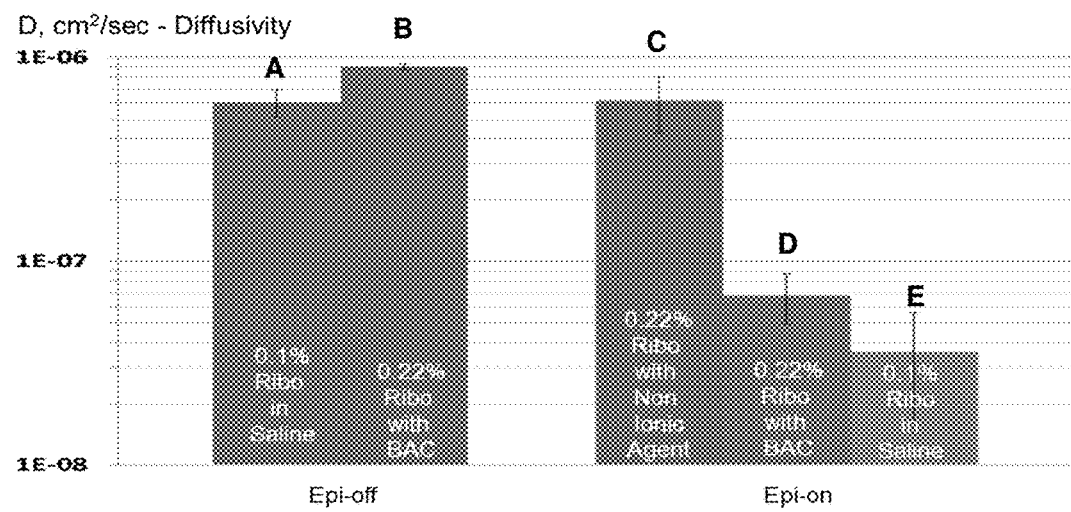
FIG. 3 illustrates relative diffusivity values for different formulations applied to corneas.

In a study, a Franz cell was employed to measure diffusivity of riboflavin formulations containing BAC or a non-ionic agent in porcine eyes with or without an epithelia of approximately 100 μm. FIG. 3 illustrates a graph of diffusivity values for the formulations in this study. Column A represents the application of a saline solution of 0.1% riboflavin to porcine eyes without epithelia (epi-off). Column B represents the application of a 0.22% riboflavin solution with BAC to porcine eyes epi-off. Column C represents the application of a 0.22% riboflavin solution with a non-ionic agent to porcine eyes with epithelia (epi-on). Column D represents the application of a 0.22% riboflavin solution with BAC to porcine eyes epi-on. Column E represents the application of a saline solution of 0.1% riboflavin to porcine eyes epi-on. The results indicates the formulation with the non-ionic agent formulation achieved faster diffusion than the ionic formulation with BAC. Furthermore, the diffusivity of the formulation with the non-ionic agent applied epi-on is similar to the diffusivity for the formulations applied epi-off. Thus, a sufficient hydrophilic/lipophilic balance was achieved with the non-ionic agent.

Study 2

In a study, porcine eyes shipped overnight on ice from an abattoir (SiouxPreme, Sioux City, Iowa) were cleaned and soaked for 20 minutes in an incubator set at 37° C. with a 0.22% riboflavin solution with BAC or a 0.22% riboflavin solution with a non-ionic agent. The corneas had epithelia of approximately 100 μm. The epithelia of the corneas were removed after the respective soaks and prior to pan-corneal irradiation with UVA light. The treatment protocol employed applying pulsed UVA light (1 second on; 1 second off) at an irradiation of 30 mW/cm$^2$ and for a dose of 7.2 J/cm$^2$, while the corneas were exposed to 100% concentration of oxygen gas. 200 μm corneal flaps were cut using a femtosecond laser. The extent of the cross-linking in the corneas was evaluated on the basis of fluorimetric analysis (excitation wave 365 nm, emission wave 450 nm) after collagen solubilization with papain.

Figure 4:
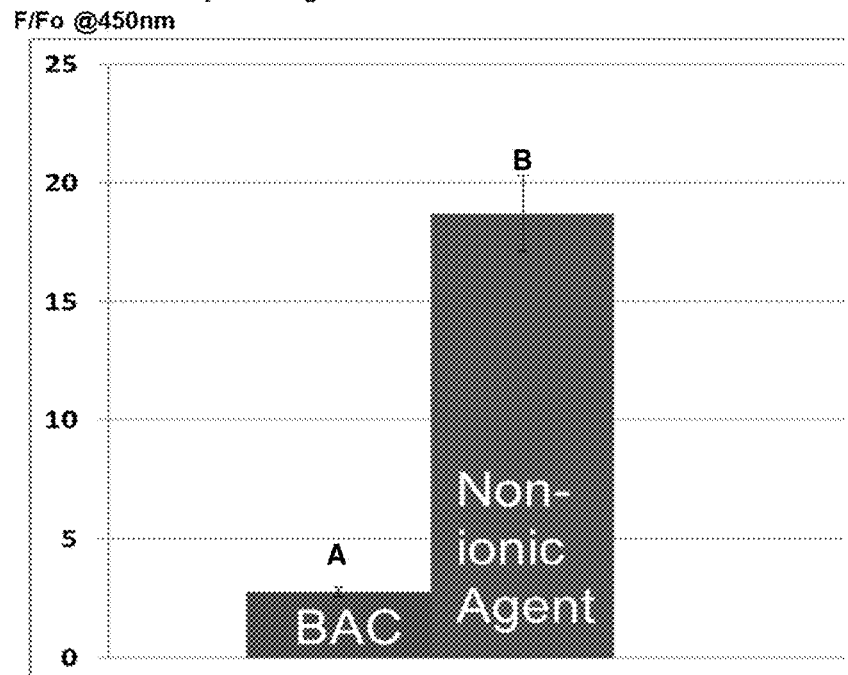
FIG. 4 illustrates relative fluorescence values for cross-linked corneas treated with different riboflavin formulations.

FIG. 4 illustrates the fluorescence values for the formulations in this study, indicating the extent of cross-linking activity. Column A represents the fluorescence of the corneas treated with the 0.22% riboflavin solution with BAC. Column B represents the fluorescence of the corneas treated with the 0.22% riboflavin solution with the non-ionic agent. The results indicate that a smaller concentration of riboflavin passed through the 100 μm epithelium and the cross-linking is riboflavin-limited when the BAC formulation was employed. In general, epi-on cross-linking requires a sufficient riboflavin concentration in the stroma to achieve greater cross-linking efficiency.

Study 3

Figures 5, 6:
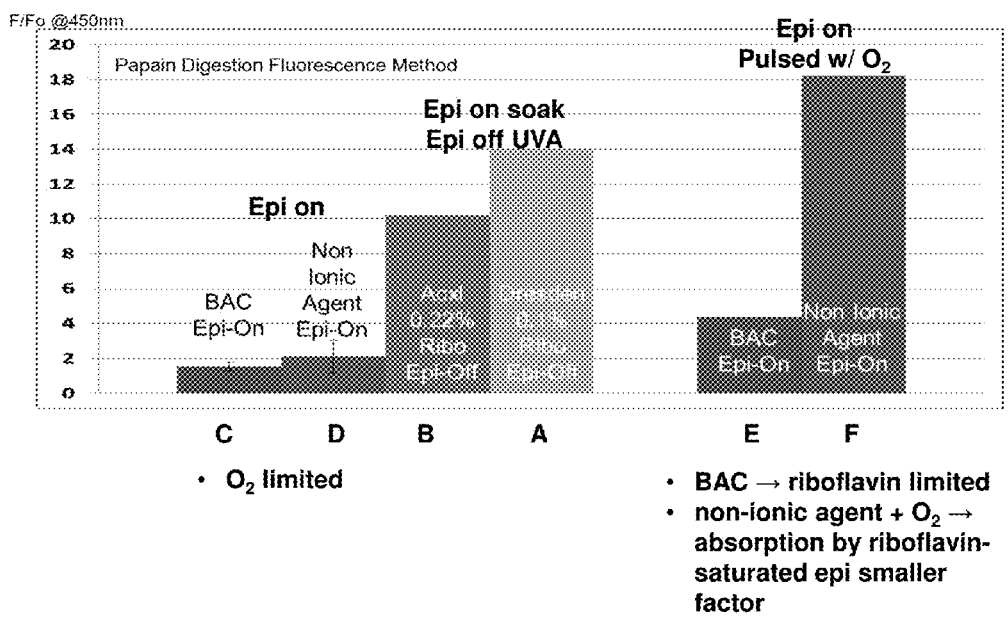
FIG. 5 illustrates different parameters for treating corneas with different riboflavin formulations.
FIG. 6 illustrates relative fluorescence values for cross-linked corneas treated according to the parameters in FIG. 16.

In a study, porcine eyes were treated according to the parameters indicated in FIG. 5. To provide a control, porcine eyes were soaked epi-off with 0.1% riboflavin solution for 20 minutes and then irradiated with continuous wave UVA light with an irradiance of 3 mW/cm$^2$ for a dose of 5.4 J/cm$^2$ while exposed to ambient air. To provide another control, porcine eyes were soaked epi-off with 0.22% riboflavin solution for 20 minutes and then irradiated with continuous wave UVA light with an irradiance of 30 mW/cm$^2$ for a dose of 7.2 J/cm$^2$ while exposed to ambient air. Additionally, porcine eyes were soaked epi-on with 0.22% riboflavin solution with BAC for 20 minutes and then irradiated with continuous wave UVA light with an irradiance of 30 mW/cm$^2$ for a dose of 7.2 J/cm$^2$ while exposed to ambient air. Porcine eyes were soaked epi-on with 0.22% riboflavin solution with a non-ionic agent for 20 minutes and then irradiated with continuous wave UVA light with an irradiance of 30 mW/cm$^2$ for a dose of 7.2 J/cm$^2$ while exposed to ambient air. Porcine eyes were soaked epi-on with 0.22% riboflavin solution with BAC for 20 minutes and then irradiated with pulsed UVA light with an irradiance of 30 mW/cm$^2$ for a dose of 7.2 J/cm$^2$ while exposed to 100% oxygen. Porcine eyes were soaked epi-on with 0.22% riboflavin solution with the non-ionic agent for 20 minutes and then irradiated with pulsed UVA light with an irradiance of 30 mW/cm² for a dose of 7.2 J/cm² while exposed to 100% oxygen.

The extent of the cross-linking in the corneas was evaluated on the basis of fluorimetric analysis. FIG. 6 shows the fluorescence values for the formulations in this study, indicating the extent of cross-linking activity. Columns A-F in FIG. 6 represent the results corresponding to the experimental parameters provided in respective rows A-F in FIG. 5. Columns C and D indicate that the cross-linking with the 0.22% riboflavin solution with BAC or the 0.22% riboflavin solution with the non-ionic agent was oxygen-limited. Columns E and F indicate that the cross-linking with the 0.22% riboflavin solution with BAC is riboflavin limited when compared to the cross-linking with the 0.22% riboflavin solution with the non-ionic agent. In addition, Columns E and F indicate that absorption by riboflavin in the saturated epithelium is not a significant factor when oxygen is applied.

In view of the foregoing, the diffusivity of riboflavin and the initial stromal concentration of riboflavin affects the extent of cross-linking activity. The results from the formulations including the non-ionic agent indicate that hydrophilic-lipophilic properties are a factor, allowing riboflavin to penetrate the epithelium and diffuse into the corneal hydrophilic stroma in quantities and duration appropriate for a clinical application.

Oxygen is a factor in efficient trans-epithelial (epi on) cross-linking. The results of the study show that the application of oxygen with the non-ionic agent provides cross-linking efficiencies similar to standard epi-off cross-linking.

Less oxygen may generally be available in the stroma due to the epithelial thickness as it relates to Fick's law of diffusion and due to photo-induced oxygen consumption in the epithelium. Thus, this study shows that the additional application of oxygen can enhance epi on cross-linking efficiency.

In addition, the absorption of UVA light by riboflavin-saturated epithelium may reduce photon efficiency. However, the results of this study indicate that, when oxygen is also applied, the absorption by riboflavin-saturated epithelium is not a predominate factor.

As described above, some riboflavin formulations include specific concentrations of Polidocanol to enhance permeability of the corneal epithelium. Advantageously, the concentrations of Polidocanol do not cause damage to the epithelium. Such riboflavin solutions may also include additives such as Fe(II).

Polidocanol and optionally additives can be employed in combination with other cross-linking techniques as described above to enhance delivery of riboflavin through the epithelium and achieve the desired amount of cross-linking activity. For instance, the riboflavin formulations with Polidocanol and optional additives can be applied with oxygen. Furthermore, the riboflavin solutions can be employed with different approaches for delivering photoactivating illumination (pulsed illumination, illumination of different patterns, etc.).

Study 4

To identify a new trans-epithelial formulation containing riboflavin, a study was conducted to test riboflavin formulations with Polidocanol as a less toxic and more efficient substitute for riboflavin formulation with benzalkonium chloride (BAC).

Pig eyes shipped overnight on ice from an abattoir (Sioux-Preme, Sioux City, Iowa) were rinsed in saline. The eyes with intact epithelium were soaked with one of the test solutions below for 20 minutes in an incubator set at 37° C. by using a rubber ring to hold the solution on top.

For a Group A of the pig eyes, the following riboflavin formulations were used:
(a1) 0.25% riboflavin solution containing BAC (PARACEL™, Avedro, Inc., Waltham, Mass.);
(a2) 0.1% w.v. riboflavin solution containing saline (PHOTREXA ZD™, Avedro, Inc., Waltham, Mass.) with added riboflavin to match the riboflavin content (0.25%) in solution (a1);
(a3) solution (a2) with 1% Polidocanol;
(a4) solution (a2) with 5% Polidocanol; and
(a5) solution (a2) with 10% Polidocanol.

The epitheliums of eyes in Group A were removed with a dull blade after the eyes were soaked in one of the solutions and irradiated pan-corneally on air with a top hat beam (3% root mean square) for 4 minutes with 365-nm light source (UV LED NCSU033B[T]; Nichia Co., Tokushima, Japan) at a chosen irradiance of 30 mW/cm² which was measured with a power sensor (model PD-300-UV; Ophir, Inc., Jerusalem, Israel) at the corneal surface. Corneal flaps (approximately 200 µm thick) were excised from the eyes with aid of an Intralase femtosecond laser (Abbot Medical Optics, Santa Ana, Calif.). The average thickness of the corneal flaps was calculated as a difference between the measurements before and after the excision from the eyes with an ultrasonic Pachymeter (DGH Technology, Exton, Pa.). The flaps were washed with distilled water and dried in a vacuum until the weight change became less than 10% (Rotary vane vacuum pump RV3 A652-01-903, BOC Edwards, West Sussex, UK). Each flap was digested for 2.5 h at 65° C. with 2.5 units/ml of papain (from Papaya latex, Sigma) in 1 ml of papain buffer [BBBS (pH 7.0-7.2), 2 mM L-cysteine and 2 mM EDTA]. Papain digests were diluted 0.5 times with 1×BBBS and fluorescence of the solutions was measured with excitation of 360 nm in a QM-40 Spectrofluorometer (Photon Technology Int., London, Ontario, Canada). The fluorescence of the papain buffer was taken into account by measuring fluorescence in the absence of tissue and subtracting this value from the fluorescence of the samples.

For a Group B of the pig eyes, the following riboflavin solutions were used:
(b1) 0.25% riboflavin solution containing BAC (PARACEL™);
(b2) 0.22% riboflavin solution containing saline (VIBEX XTRA™, Avedro, Inc., Waltham, Mass.) with 1% Polidocanol;
(b3) 0.22% riboflavin solution containing saline (VIBEX XTRA™) with 5% Polidocanol; and
(b4) 0.22% riboflavin solution containing saline (VIBEX XTRA™).

The epitheliums of eyes in Group B were not removed after soaking in one of the solutions and the surfaces were briefly rinsed with a saline buffer before irradiation. The epitheliums were removed after the irradiation. Conditions used for the irradiation and the following treatment of the eyes were the same as for Group A.

For a Group C of the pig eyes, the following riboflavin solutions were used:
(c1) 0.25% riboflavin solution containing BAC (PARACEL™);
(c2) 0.22% riboflavin solution containing saline (VIBEX XTRA™) with 1% Polidocanol; and
(c3) 0.22% riboflavin solution containing saline (VIBEX XTRA™) with 3% Polidocanol.

The epitheliums of eyes in Group C were not removed after soaking in one of the solutions and the surfaces were briefly rinsed with a saline buffer before irradiation. The eyes were placed in a beaker with an oxygen stream for 2 minutes in the incubation chamber prior to irradiation. Corneas were pan-corneally irradiated with irradiance of 30 mW/cm$^2$, pulsed 1 sec on: 1 sec off for a total time of 8 min (7.2 J). The eyes were exposed to oxygen during all time of the treatment. The epithelium were removed from the cornea after the irradiation with a dull blade. Corneal flaps (approximately 200 μm thick) were excised from the eyes with aid of Intralase femtosecond laser and the following treatment of the flaps was the same as for the Groups A and B.

For a Group D and a Group E of the pig eyes, the following riboflavin solutions were used:
 (d1) 0.25% riboflavin solution containing BAC (PARACEL™);
 (d2) 0.22% riboflavin solution containing saline (VIBEX XTRA™) with 1% Polidocanol;
 (d3) 0.22% riboflavin solution containing saline (VIBEX XTRA™) with 1% Polidocanol and 2.5 mM Fe(II).
 (d4) 0.22% riboflavin solution containing saline (VIBEX XTRA™) with 3% Polidocanol; and
 (d5) 0.22% riboflavin solution containing saline (VIBEX XTRA™) with 3% Polidocanol and 2.5 mM Fe(II).

For Group D, the experimental procedure (including the irradiation, oxygen exposure, and the cutting of the flaps) was the same as for Group C.

The epitheliums of eyes in Group E were removed after soaking in one of the solutions for 20 min. The eyes then were placed in a beaker with oxygen stream for 2 minutes in the incubation chamber prior to irradiation. Corneas were pan-corneally irradiated with irradiance of 30 mW/cm$^2$, pulsed 1 sec on: 1 sec off for total time of 8 min (7.2 J). The eyes were exposed to oxygen during all time of the treatment. Corneal flaps (approximately 200 μm thick) were excised from the eyes with aid of Intralase femtosecond laser and the following treatment of the flaps was the same as for the Groups A and B.

FIGS. 7-15 illustrate the cross-linking activity induced in Groups A-E by various riboflavin solutions. The cross-linking activity was measured as a ratio of fluorescence for the treated sample (F) to fluorescence for an untreated control (Fo), where emissions were recorded at a wavelength of 450 nm. Such measurement of cross-linking activity is described, for example, in U.S. Pat. No. 9,020,580, filed Jun. 4, 2012 and titled "Systems and Methods for Monitoring Time Based Photo Active Agent Delivery or Photo Active Marker Presence," the contents of which are incorporated entirely herein by reference.

Figure 7:
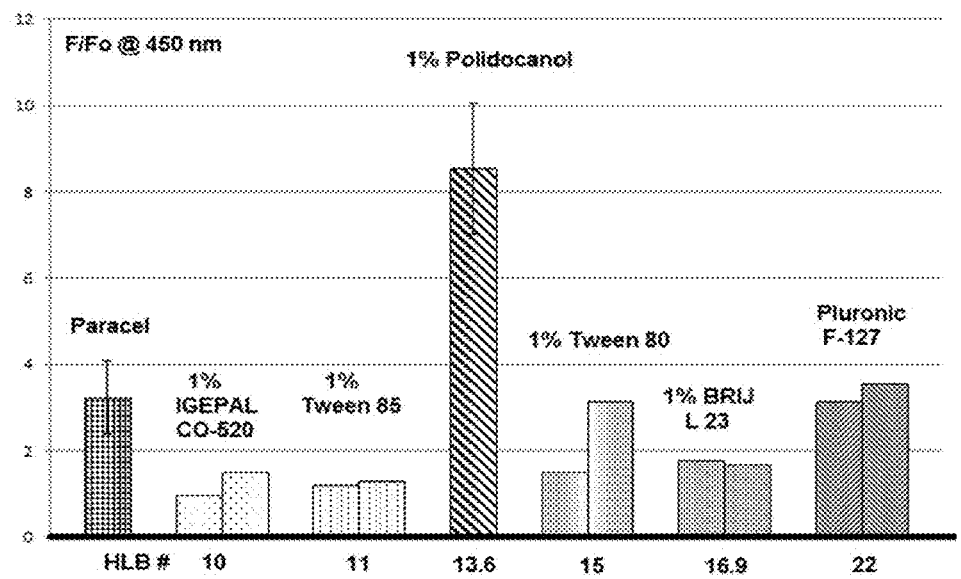
FIG. 7 illustrates relative fluorescence for cross-linked conical flaps treated with different surfactants in riboflavin solution.
Figure 8:
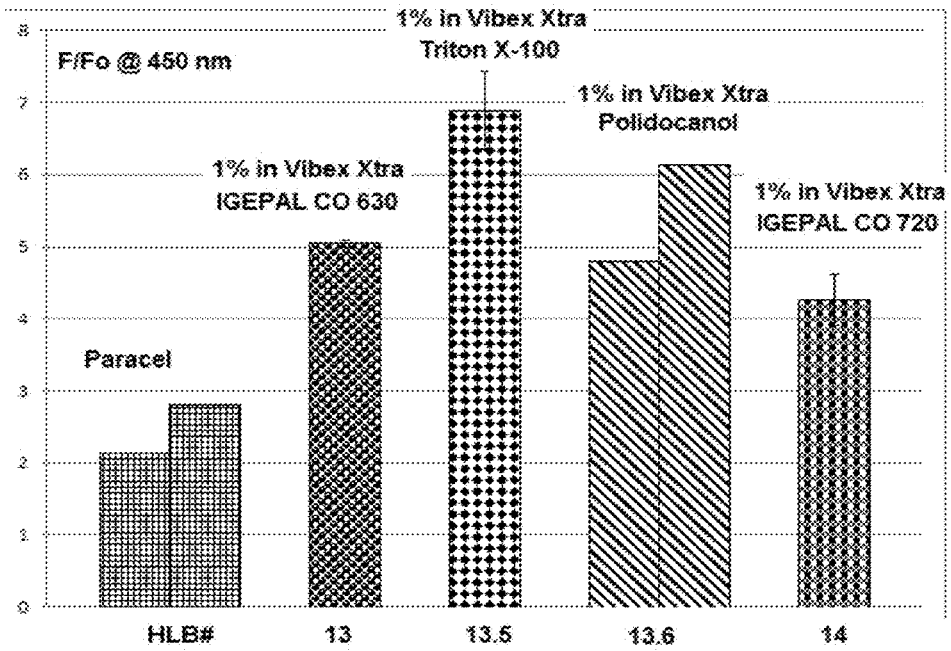
FIG. 8 illustrates relative fluorescence for cross-linked conical flaps treated with different surfactants in riboflavin solution.

FIGS. 7 and 8 illustrate relative fluorescence for cross-linked corneal flaps treated with different surfactants in 0.22% riboflavin solution containing saline (VIBEX XTRA™) applied topically to pig eyes with intact epithelium for 20 min, after which the epithelium were then removed and the eyes were irradiated with 30 mW/cm$^2$ for 4 min. These results are presented in relation to corneal flaps treated with 0.25% riboflavin solution containing BAC (PARACEL™) under the same procedural conditions.

Figure 9:
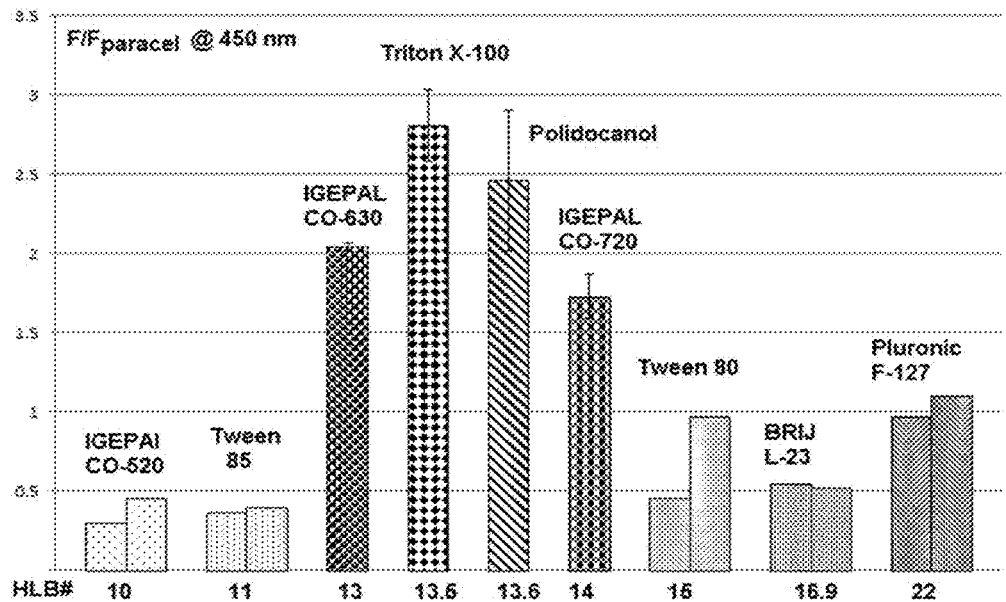
FIG. 9 illustrates relative fluorescence for cross-linked conical flaps treated with different surfactants in riboflavin solution.

FIG. 9 illustrates relative fluorescence for cross-linked corneal flaps after using 1% solutions of different surfactants in 0.22% riboflavin solution containing saline (VIBEX XTRA™). These results are presented in relation to the fluorescence from corneal flaps treated with only 0.25% riboflavin solution containing BAC (PARACEL™) in the same procedural conditions. FIGS. 7-9 also show the HLB numbers for the surfactants, e.g., Polidocanol has an HLB number of 13.6.

Figure 10:
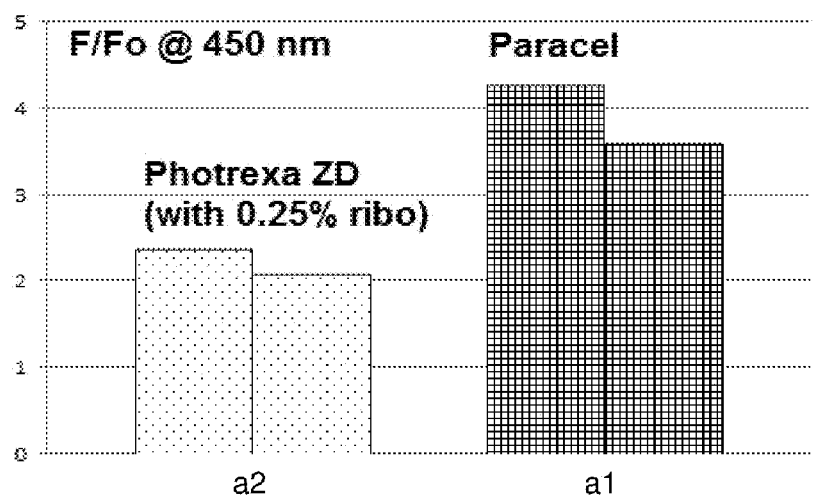
FIG. 10 illustrates relative fluorescence for cross-linked conical flaps treated with a riboflavin solution that does not include benzalkonium chloride (BAC), relative to a riboflavin solution that includes BAC as a permeability enhancer.
Figure 11:
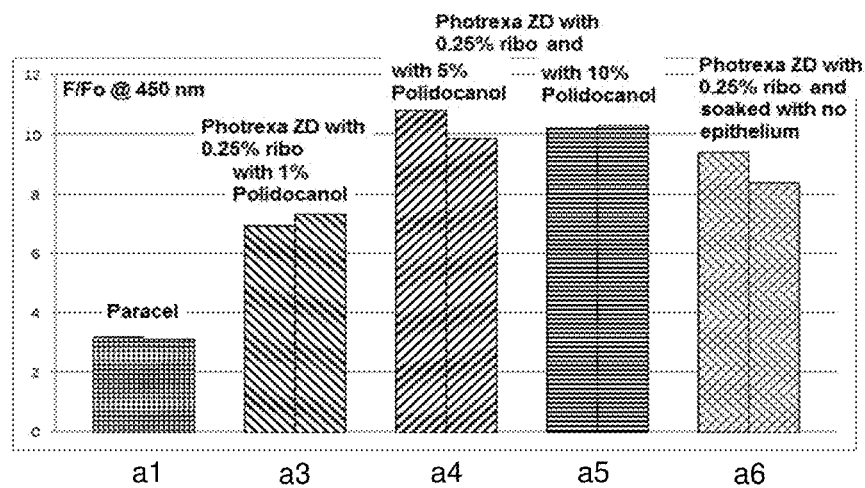
FIG. 11 illustrates relative fluorescence for cross-linked conical flaps treated with riboflavin solutions that include different concentrations of Polidocanol as a permeability enhancer, relative to other riboflavin solutions that include BAC as a permeability enhancer and to other riboflavin solutions without any permeability enhancer.

For Group A, FIG. 10 illustrates relative fluorescence for cross-linked corneal flaps treated with solution (a2) which does not include BAC relative to solution (a1) which includes BAC. Meanwhile, FIG. 11 illustrates relative fluorescence of cross-linked corneal flaps treated with solutions (a3), (a4), and (a5) which include different concentrations of Polidocanol. These results are presented relative to corneal flaps treated with solution (a1) which includes BAC and corneal flaps with no epithelium treated with solution (a2) which does not include Polidocanol or BAC.

Figure 12:
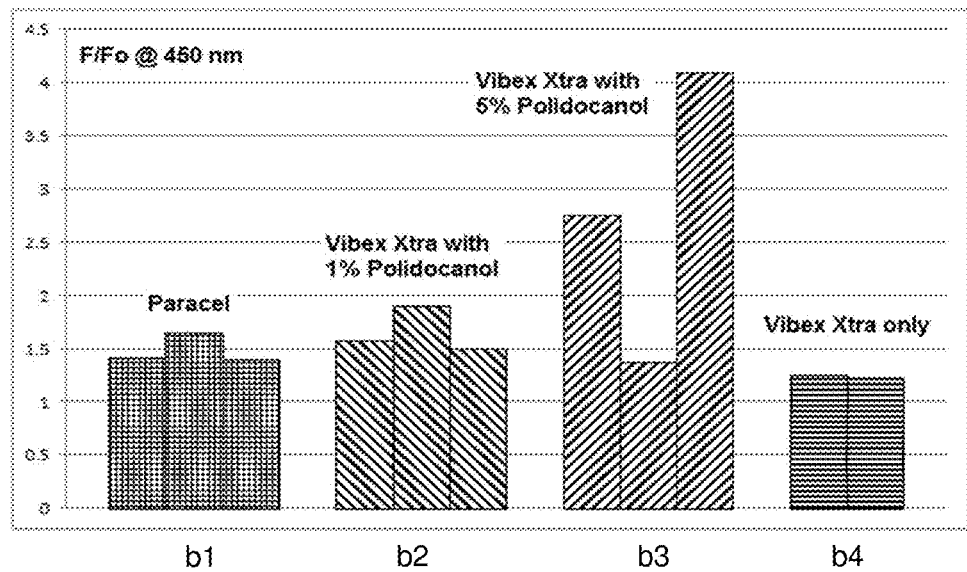
FIG. 12 illustrates relative fluorescence for cross-linked conical flaps treated with riboflavin solutions that include different concentrations of Polidocanol as a permeability enhancer, relative to other riboflavin solutions that include BAC as a permeability enhancer and to other riboflavin solutions without any permeability enhancer.

For Group B, FIG. 12 illustrates relative fluorescence for cross-linked corneal flaps treated with solutions (b2) and (b3) which include 1% and 5% concentrations of Polidocanol respectively. These results are presented relative to corneal flaps treated with solution (b1) which includes BAC and corneal flaps treated with solution (b4) which does not include Polidocanol or BAC.

Figure 13:
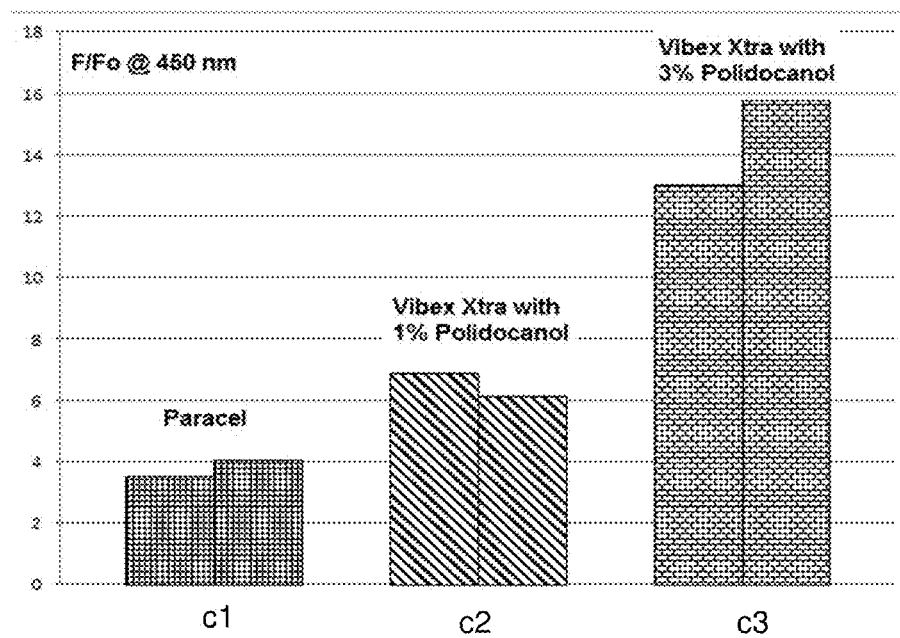
FIG. 13 illustrates relative fluorescence for cross-linked conical flaps treated with riboflavin solutions that include different concentrations of Polidocanol as a permeability enhancer, relative to other riboflavin solutions that include BAC as a permeability enhancer and to other riboflavin solutions without any permeability enhancer.

For Group C, FIG. 13 illustrates relative fluorescence of cross-linked corneal flaps treated with solutions (c2) and (c3) which include 1% and 3% concentrations of Polidocanol respectively. These results are presented relative to corneal flaps treated with solution (c1) which includes BAC.

Figure 14:
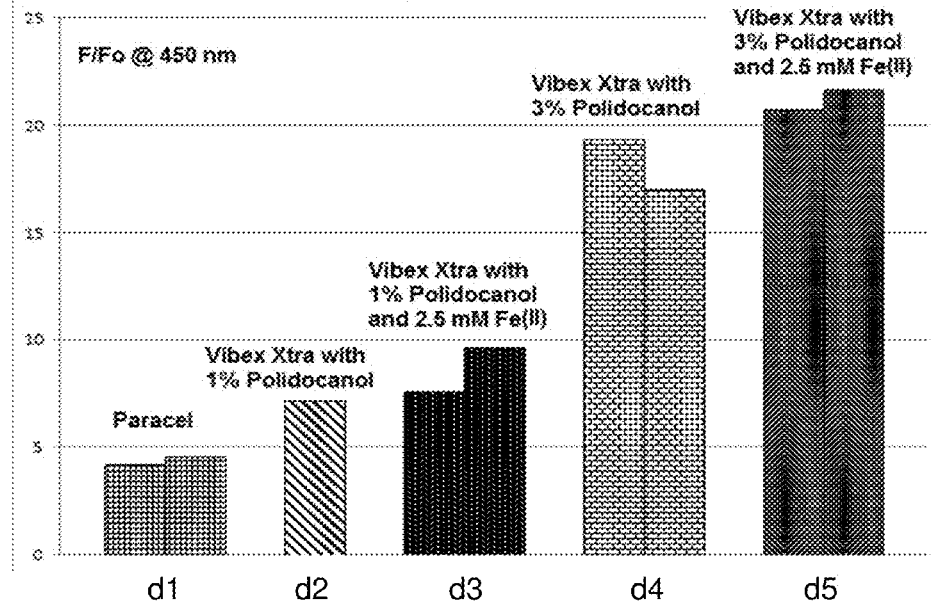
FIG. 14 illustrates relative fluorescence for cross-linked conical flaps treated with riboflavin solutions that include different concentrations of Polidocanol as a permeability enhancer or riboflavin solutions that include different concentrations of Polidocanol as well as Fe(II) as an additive, relative to other riboflavin solutions that include BAC as a permeability enhancer.
Figure 15:
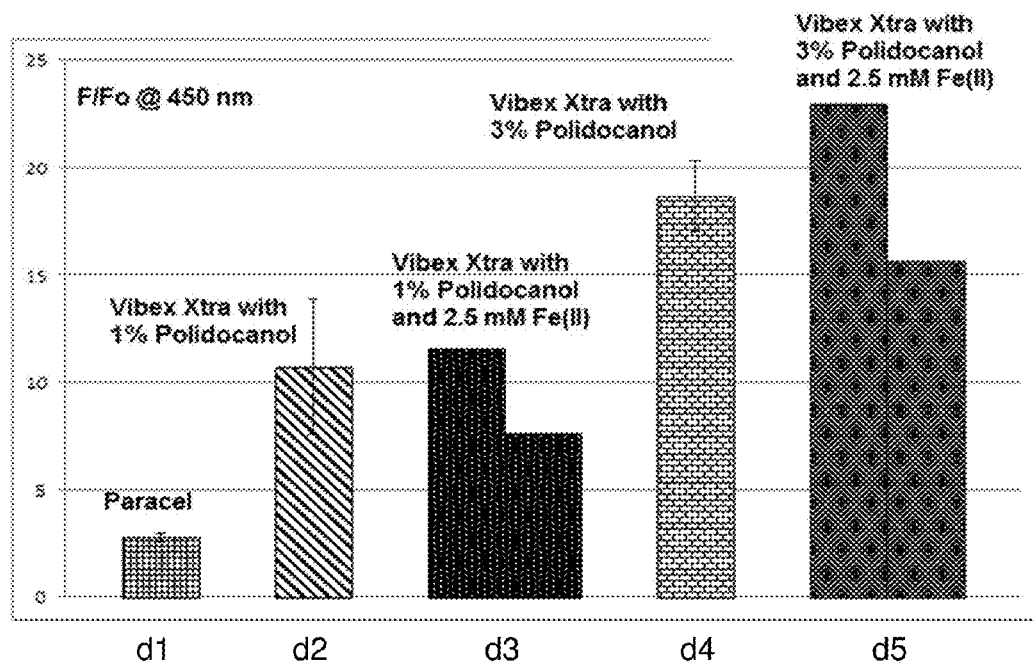
FIG. 15 illustrates relative fluorescence for cross-linked conical flaps treated with riboflavin solutions that include different concentrations of Polidocanol as a permeability enhancer or riboflavin solutions that include different concentrations of Polidocanol as well as Fe(II) as an additive, relative to other riboflavin solutions that include BAC as a permeability enhancer.

FIG. 14 for Group D and FIG. 15 for Group E illustrate relative fluorescence of cross-linked flaps treated with solutions (d2) and (d4) which include 1% and 3% concentrations of Polidocanol respectively and with solutions (d3) and (d5) which include 2.5 mM iron(II) as well as 1% and 3% concentrations of Polidocanol respectively. These results are presented relative to corneal flaps treated with solution (d1) which includes BAC. As described above, the epitheliums in Group D were not removed after soaking in the solutions, while the epitheliums in Group E were removed after soaking in the solutions.

As the results of the study show, the inventors have identified Polidocanol as a non-ionic surfactant that is more effective than many other surfactants for enhancing permeability and generating cross-linking activity. Although the use of BAC in riboflavin solutions may help riboflavin to pass through the epithelium, Polidocanol is far more effective and efficient than BAC in enhancing permeability in the epithelium and generating cross-linking activity. Advantageously, non-ionic agents, such as Polidocanol, are less corrosive and damaging to the epithelium than BAC.

Study 5

As described above, several permeability enhancers may be combined to achieve a specific HLB that achieves more optimal permeability for the epithelium. A study was conducted to test combinations of surfactants with different HLB numbers.

Intact epithelium were soaked for 20 min using one of the following solutions:
 (e1) 0.25% riboflavin solution containing BAC (PARACEL™);
 (e2) 0.22% riboflavin solution containing saline (VIBEX XTRA™) with 1% IGEPAL CO-630;
 (e3) 0.22% riboflavin solution containing saline (VIBEX XTRA™) with 1% IGEPAL CO-720; and
 (e4) 0.22% riboflavin solution containing saline (VIBEX XTRA™) with 1% mixture of IGEPAL CO-630 with IGEPAL CO-720 (1:1 ratio).

The epitheliums of the eyes were removed and the eyes were irradiated with 30 mW/cm$^2$ for 4 min continuously on air. Corneal flaps with thickness of 200 μm were cut and the papain digestion and fluorescence analysis was conducted as previously described above.

Figure 16:
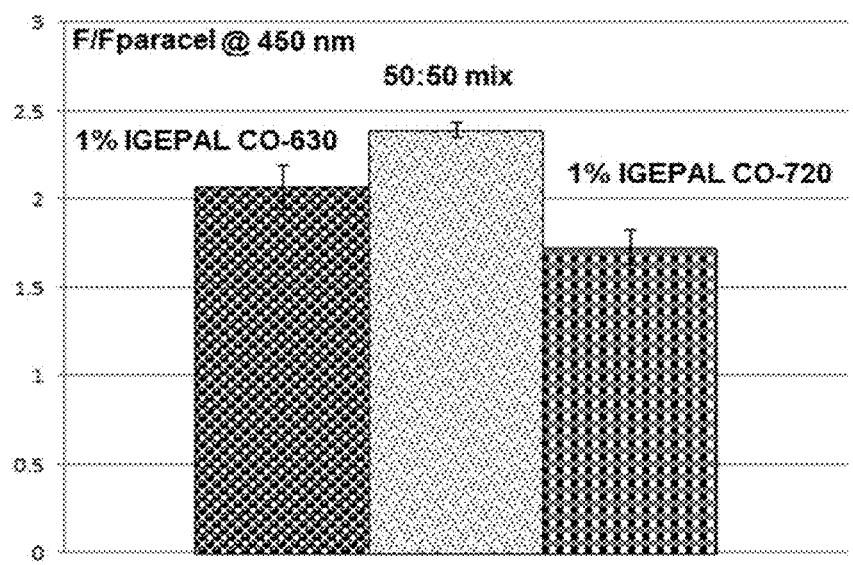
FIG. 16 illustrates relative fluorescence of cross-linked flaps treated with one of two different surfactants or a combination of the two surfactants.

FIG. 16 illustrates relative fluorescence of the cross-linked flaps treated with one of two different surfactants or a combination of the two surfactants. The cross-linking activity was measured as a ratio of fluorescence for the respective treated sample (F) to fluorescence for a sample treated with solution (e1) (Fparacel), where emissions were recorded at a wavelength of 450 nm.

The surfactant IGEPAL CO-630 has a HLB number of 13 and the surfactant IGEPAL CO-720 has a HLB number of 14, the 1:1 mixture has a HLB number of 13.5. As FIG. 16 shows, the mixture of the surfactants facilitates riboflavin permeation through the corneal epithelium more effectively than the surfactants employed individually.

Although the examples described herein may relate to the use of riboflavin and Polidocanol as a permeability enhancer for corneal cross-linking treatments, it is understood that other photosensitizers and/or other permeability enhancers (e.g., non-ionic surfactant with an appropriate HLD number) may be employed. Furthermore, other types of treatment are contemplated, such as antimicrobial photodynamic therapy, where enhanced or controlled delivery of a photosensitizer through an epithelium may be advantageous.

As described above, the example treatment system 100 includes the applicator 132, which may be an eye dropper, syringe, or the like from which a cross-linking agent solution can be dripped onto the cornea. When the cross-linking agent solution is applied broadly as eye drops, many parts of the eye and areas surrounding the eye are exposed to the solution. Although the cross-linking agent solution may be applied to treat a specific portion of the cornea, other portions of the cornea and non-corneal tissue may also be exposed to the cross-linking agent solution.

As also described above, one formulation for cross-linking treatment includes BAC to enhance trans-epithelial delivery. In addition to being corrosive to the epithelium, BAC can irritate other tissues of the eye as well as areas surrounding the eye. In general, using devices (e.g., eye droppers) that broadly apply formulations including irritating agents (e.g., BAC) may affect tissues that are not targeted for treatment.

Figure 17:
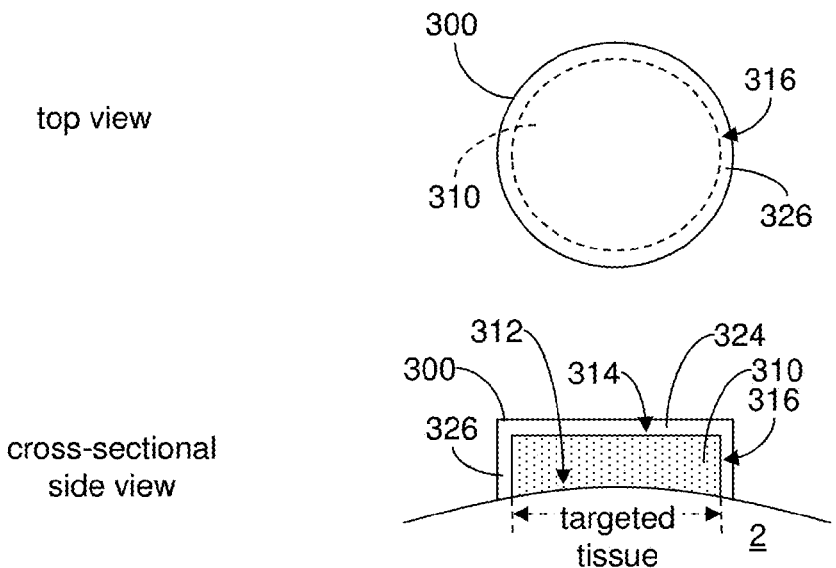
FIG. 17 illustrates an example device for focally delivering a drug to a cornea of an eye according to aspects of the present disclosure.

FIG. 17 illustrates a top view and a cross-sectional side view of an example drug delivery device 300 that can apply a cross-linking agent solution focally to areas of the cornea 2 targeted for cross-linking treatment. The system 100 or device 200 described above may be employed to photoactivate the cross-linking agent applied by the delivery device 300 to generate the desired cross-linking activity. Although the delivery device 300 may apply any of the cross-linking agent formulations described above, the delivery device 300 is particularly advantageous when applying formulations including an irritating agent, such as BAC. By delivering such formulations focally to targeted areas of the cornea 2, the delivery device 300 helps to keep non-targeted tissues from being exposed to the irritating agents.

The delivery device 300 includes a drug-eluting element 310. The drug-eluting element 310 is formed from a material that can be loaded with (e.g., be saturated with) the cross-linking agent solution. When the delivery device 300 is applied to the eye 1, the drug-eluting element 310 is positioned over areas of the cornea 2 targeted for cross-linking treatment. The corneal tissue in the targeted areas can then absorb the cross-linking agent solution from the drug-eluting element 310.

The drug-eluting element 310 has a bottom outer surface 312, a top outer surface 314, and a side outer surface 316. The bottom surface 312 and the top surface 314 are on opposing ends of the drug-eluting element 310, and the side surface 316 extends around the drug-eluting element 310 between the bottom surface 312 and the top surface 314. The bottom surface 312 defines a substantially circular area. The bottom surface 312 can thus be applied to release a cross-linking agent solution to a corresponding circular area of the cornea 2 where cross-linking treatment is desired. The top surface 314 may also be substantially circular.

In general, however, the drug-eluting elements described herein may vary in shape and size depending on the desired treatment and the shape of the targeted tissue. For instance, the bottom surface 312 may have an alternative shape that can deliver the cross-linking agent to an elliptical, annular, bowtie, trapezoidal or rectangular treatment area. Additionally, aspects of the bottom surface 312 may be contoured to accommodate the surface shape of the targeted tissue.

The drug-eluting element 310 may be formed as a polyvinyl alcohol (PVA) sponge. Alternatively, the drug-eluting element 310 may be formed from a hydrogel, a methylcellulose-based polymer, collagen, or the like. The drug-eluting element 310 may have a texture that provides specific surface tension at the surface of the targeted tissue based on the viscosity of the drug.

The drug-eluting element 310 may have a diffusivity to allow the drug to be released to the targeted tissue at a specific rate. Alternatively or additionally, the drug-eluting element 310 may have hydrophilic/hydrophobic and/or lipophobic/lipophilic properties that allow the drug to be released to the targeted tissue at a specific rate. Alternatively, the drug-eluting element 310 may have pore sizes that allow the drug to be released to the targeted tissue at a specific rate. Additionally or alternatively, the drug-eluting element 310 may include a number of dissolving layers that allow the drug to be released to the targeted tissue at a specific rate.

If the drug-eluting element 310 is sponge-like with pores, the following theory may apply for the flow of the drug from the drug-eluting element 310:

Diffusion fluxes of a liquid inside the porous medium (q) and inside a pore (q*) are expressed as follows:

$$q = D' \frac{dc}{dx} \tag{1}$$

$$q^* = D \frac{dc}{dl} \tag{2}$$

where x and l are coordinates which are normal or parallel in respect to a pore.

Coefficient of tortuousness (τ) is expressed as the following ratio:

$$\tau = \frac{dl}{dx} \tag{3}$$

$$\frac{dc}{dl} = \frac{dc}{dx}\frac{dx}{dl} = \frac{dc}{dx}\frac{1}{\tau} \tag{4}$$

If h is the average diameter of pores and N is number of pores per unit of square, then the total flux (q) can be expressed as follows:

$$q = q^* N \frac{\pi h^2}{4} = N \frac{\pi h^2}{4} D \frac{dc}{dl} = ND \frac{\pi h^2}{4} \frac{dc}{dx} \tag{5}$$

Comparing (5) and (1), the diffusion coefficient inside the porous material is directly proportional to the number of pores and their diameter (in power two) and inversely to the level of tortuousness:

$$D' = D \frac{N}{\tau} \frac{\pi h^2}{4} \quad (6)$$

When the average diameter of the pores becomes large enough, the volumetric flow ($q_v$) is governed by Poiseuille's law:

$$q_V = \frac{\pi R^4 \Delta P}{8\mu L} = \frac{\pi h^4 \rho g}{128\mu\tau} \quad (7)$$

where g is the standard gravity, ρ is the fluid density, and μ is the dynamic fluid viscosity.

The delivery device 300 also includes one or more barrier structures that are formed along one or more surfaces of the drug-eluting element 310. In particular, a top barrier 324 is formed over the top surface 314 and a side barrier 326 is formed around the side surface 316. Although the barriers 324, 326 appear as thin structures in FIG. 17, barrier structures of various shapes and sizes (e.g., thicknesses) may be employed depending on the desired treatment. Examples of different barrier structures are shown, for instance, in FIGS. 18 and 19, described in detail below.

The barriers 324, 326 are formed from one or more materials that help to prevent or inhibit the release of the cross-linking agent solution from the drug-eluting element 310 through the top surface 314 and the side surface 316. The barriers 324, 326 help to ensure that the cross-linking agent solution is directed primarily through the bottom surface 312 to the area of the cornea 2 targeted for treatment. In other words, the bottom surface 312 acts as a delivery surface which can be positioned against the cornea 2 and is shaped to define the area of the cornea 2 targeted for treatment. Responsive to the bottom surface 312 being positioned against the cornea 2, the drug-eluting element 310 releases the drug to the area of targeted tissue through the bottom surface. In contrast, the top surface 314 and the side surface 316 are non-delivery surfaces due to the barriers 324, 326.

Depending on the drug delivered by the drug delivery device 300, the drug-eluting element 310 and the barriers 324, 326 are formed from respective materials with the appropriate hydrophilic/hydrophobic and/or lipophobic/lipophilic properties. For instance, the barriers 324, 326 are formed from materials with particular hydrophilic/hydrophobic and/or lipophobic/lipophilic properties to separate non-targeted tissue from the drug-eluting element 310.

In some cases, the drug-eluting element 310 and the drug both have hydrophilic/hydrophobic and/or lipophobic/lipophilic properties that are opposite from the properties of the barriers 324, 326. For instance, if the delivery device 300 is employed to deliver a riboflavin solution which is hydrophilic, the drug-eluting element 310 may also be hydrophilic so that it can receive the riboflavin solution while the barriers 324, 326 may be hydrophobic to repel the riboflavin solution.

The drug-eluting element 310 and/or the barriers 324, 326 may have a texture that provides a specific mechanical surface modification when the drug-eluting element is in contact with tissue. The mechanical surface modification may occur in response to a range of applied forces. Additionally or alternatively, the mechanical surface modification may occur in response to an applied frequency. Additionally or alternatively, the mechanical surface modification may occur in response to the movement of the drug-eluting material across the surface of the targeted tissue for a specified distance.

Figure 18:
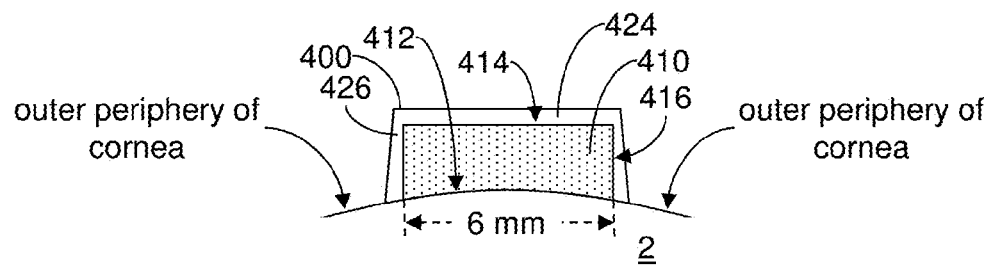
FIG. 18 illustrates another example device for focally delivering a drug to a cornea of an eye according to aspects of the present disclosure.

FIG. 18 illustrates another example drug delivery device 400. The delivery device 400 includes a drug-eluting element 410 and barriers 424, 426. The drug-eluting element 410 has a bottom outer surface 412, a top outer surface 414, and a side outer surface 416. The bottom surface 412 and the top surface 414 are on opposing ends of the drug-eluting element 410, and the side surface 416 extends around the drug-eluting element 410 between the bottom surface 412 and the top surface 414. The bottom surface 412 and the top surface 414 may be substantially circular. As shown, the bottom surface 412 may be shaped to apply a cross-linking agent solution to a circular area with a diameter of approximately 6 mm at the corneal surface. If the cornea has a diameter of approximately 11.5 mm, for instance, the drug-eluting element 410 delivers the cross-linking agent solution only to a central portion of the cornea 2.

The top barrier 424 is formed over the top surface 414 and the side barrier 426 is formed around the side surface 416. The barriers 424, 426 are formed from a material that helps to prevent or inhibit the release of the cross-linking agent solution from the drug-eluting element 410 through the top surface 414 and the side surface 416. In this example, the bottom surface 412 acts as a delivery surface, while the top surface 414 and the side surface 416 act as non-delivery surfaces.

In contrast to the side barrier 326 in FIG. 17, the side barrier 426 increases in thickness as it extends downwardly from the top barrier 424 to the bottom surface 412. The side barrier 426 has an outer surface that slopes radially outward with the increasing thickness. In effect, the side barrier 426 forms a tapered skirt around the drug-eluting element 410.

As shown in FIG. 18, the outer periphery of the cornea 2 is disposed beyond the side barrier 426 and remains uncovered by the delivery device 400. If the side barrier 426 is formed from a hydrophobic material, for instance, lubricating drops can be applied to the outer surface of the side barrier 426. The lubricating drops can flow along the outer surface of the side barrier 426 to the outer periphery of the cornea to keep the cornea and conjunctiva/sclera hydrated, especially when an eye speculum is implemented and the eye remains open for an extend length of time. The lubricating drops can also rinse away any cross-linking agent solution that may seep under the side barrier 426 along the corneal surface and to the outer periphery. The lubricating drops provide irrigation of the outer periphery of the cornea 2, without affecting (e.g., diluting) the cross-linking agent solution delivered from the drug-eluting element 410 to the targeted corneal tissue. In other words, the side barrier 426 helps to prevent the flow of the lubricating drops to the drug-eluting element 410 or the targeted tissue at the central portion of the cornea 2.

Figure 19:
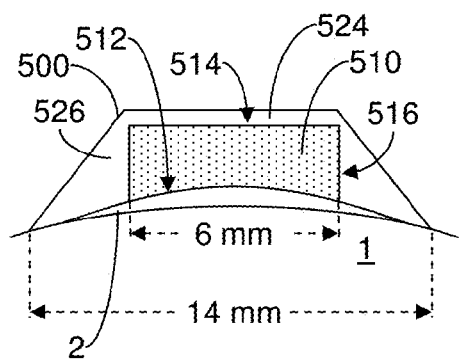
FIG. 19 illustrates yet another example device for focally delivering a drug to a cornea of an eye according to aspects of the present disclosure.

FIG. 19 illustrates yet another example drug delivery device 500. The delivery device 500 includes a drug-eluting element 510 and barriers 524, 526. The drug-eluting element 510 has a bottom outer surface 512, a top outer surface 514, and a side outer surface 516. The bottom surface 512 and the top surface 514 are on opposing ends of the drug-eluting element 510, and the side surface 516 extends around the drug-eluting element 510 between the bottom surface 512 and the top surface 514. The bottom surface 512 and the top surface 514 may be substantially circular. Like the drug-eluting element 410 of FIG. 18, the bottom surface 512 may be shaped to deliver a cross-linking agent solution to a central circular area with a diameter of approximately 6 mm at the corneal surface.

The top barrier 524 is formed over the top surface 514 and the side barrier 526 is formed around the side surface 516. The barriers 524, 526 are formed from a material that helps to prevent or inhibit the release of the cross-linking agent solution from the drug-eluting element 510 through the top surface 514 and the side surface 516. In this example, the bottom surface 512 acts as a delivery surface, while the top surface 514 and the side surface 516 act as non-delivery surfaces.

The side barrier 526 increases in thickness as it extends downwardly from the top barrier 524 to the bottom surface 512. The side barrier 526 has an outer surface that slopes radially outward with the increasing thickness. Unlike the side barrier 426 in FIG. 18, the side barrier 526 extends outwardly a greater distance to form a larger skirt around the drug-eluting element 510, for instance, with a diameter of approximately 14 mm. If the cornea has a diameter of approximately 11.5 mm, for instance, the side barrier 526 extends past the limbus and to other structural features (e.g., sclera, conjunctiva, etc.) beyond the diameter when the drug-delivery device 500 is applied to the eye 1. In general, the side barrier 526 may extend to a maximum diameter of greater than approximately 11.5 mm around the bottom surface 512, while the side barrier 426 may extend to a maximum diameter of between approximately 6 mm and approximately 11.5 mm around the bottom surface 412. Unlike the drug-delivery device 400 above, the drug-delivery device 500 covers the entire cornea 2 and helps to keep the outer periphery of the cornea 2 (beyond the drug-eluting element 510) hydrated. If, for instance, the barriers 524, 526 are formed from a hydrophobic material and the drug is a hydrophilic riboflavin solution, surface tension helps to prevent the riboflavin solution from travelling, via capillary action, between the side barrier 526 and the surface of the eye 1 and away from the targeted tissue.

Although the treatment systems and devices above are described in the context of cross-linking treatments, such treatment systems and devices may be additionally or alternatively used to provide other eye treatments. For instance, focal drug delivery may be employed to treat corneas and/or other specific anterior eye tissues suffering from infections such as ulcers caused by viral or bacterial pathogens. Indeed, the drug delivery devices 300, 400, 500 may also apply a photosensitizer, such as riboflavin, for the antimicrobial effect that is generated when the photosensitizer is activated by light, e.g., by the system 100 or device 200 described above.

Although the shapes of the delivery surfaces described above may be substantially circular, it is understood that the delivery surfaces may have other shapes, e.g., elliptical, annular, bowtie, trapezoidal or rectangular etc. In general, the delivery surface determines one or more areas of targeted tissue to receive a drug. One or more barriers may be employed to define a delivery surface with a desired shape. For instance, a smaller circular barrier may be applied at the center of a larger circular surface of a drug-eluting element to define a delivery surface with an annular shape, where the barrier inhibits flow of the drug from the center of the larger circular surface.

Figure 20:
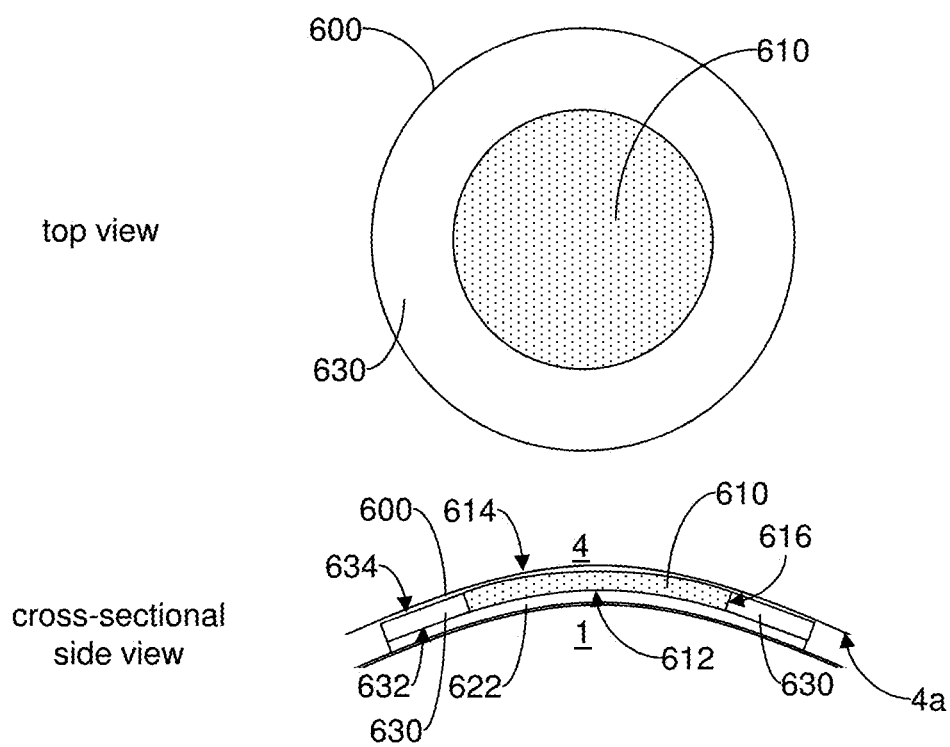
FIG. 20 illustrates an example device for focally delivering a drug to an eyelid according to aspects of the present disclosure.

Furthermore, the targeted tissues are not limited to corneal tissue. For instance, FIG. 20 illustrates a top view and a side cross-sectional view of another example drug delivery device 600 for focally delivering a drug to the eyelid 4 of an eye 1. For instance, an antimicrobial drug may be applied to the eyelid 4 to treat a bacterial infection. The delivery device 600 includes a drug-eluting element 610, which is formed from a material that can be loaded with the drug for treating the eyelid 4. The drug-eluting element 610 has a bottom outer surface 612, a top outer surface 614, and a side outer surface 616. When the delivery device 600 is applied to the eye 1, the drug-eluting element 610 is positioned between the eye 1 and the inside surface of the eyelid 4. The top surface 614 contacts the inner surface 4a of the eyelid 4. The tissue along the inner surface 4a can then absorb the drug from the drug-eluting element 410 through the top surface 614. As shown in the top view, the top surface 614 releases the drug from a substantially circular area, although differently shaped areas may be employed.

The delivery device 600 also includes a bottom barrier 622. When the delivery device 600 is applied to the eye 1, the bottom barrier 622 covers a portion of the eye 1 and is positioned between the eye 1 and the drug-eluting element 610. The bottom surface 612 of the drug-eluting element 610 is positioned along the bottom barrier 622. The bottom barrier 622 is formed from a material that helps to prevent the release of the drug through the bottom surface 612 to the non-targeted tissues of the eye 1. Advantageously, the bottom barrier 622 minimizes the exposure of the eye 1 to any irritating agents in the drug.

As described above, the drug-eluting element 610 and the bottom barrier 622 are formed from respective materials with the appropriate hydrophilic/hydrophobic and/or lipophobic/lipophilic properties. For instance, the bottom barrier 622 is formed from materials with particular hydrophilic/hydrophobic and/or lipophobic/lipophilic properties to separate non-targeted tissue, e.g., the eye 1, from the drug-eluting element 610. In some cases, the drug-eluting element 610 and the drug both have hydrophilic/hydrophobic and/or lipophobic/lipophilic properties that are opposite from the properties of the bottom barrier 622.

In addition, the drug delivery device 600 may include a scrubber skirt 630 disposed around the side surface 616. As shown in the top view of FIG. 20, the scrubber skirt 630 has a substantially annular shape, although different shapes may be employed. The scrubber skirt 630 includes a bottom surface 632 and a top surface 634. The bottom surface 632 is positioned along the bottom barrier 622. The top surface 634 may be textured to scrub the inner surface 4a of the eyelid 4 as the eyelid 4 moves over the scrubber skirt 630. As such, the treatment of the eyelid 4 combines: (i) scrubbing the affected tissue with the scrubber skirt 630, and (ii) applying the drug to the affected tissue with the drug-eluting element 610. As such, the delivery device 600 may be employed to treat meibomian gland dysfunction, where the scrubbing can remove oil, bacteria and debris and stimulate the oil glands. In some cases, the scrubber skirt 630 may be formed from a lipophilic material to enhance the effect of scrubbing the inner surface 4a. In other cases, the scrubber skirt 630 may also act like the drug-eluting element 610 to apply the drug to the inner surface 4a.

As described above, the drug-eluting element 610 and the bottom barrier 622 are formed from respective materials with the appropriate hydrophilic/hydrophobic and/or lipophobic/lipophilic properties. Additionally, the device may also have a deformable hinge that allows the device to wrap around the entire eyelid, the deformed hinge providing sufficient force to hold the device in place. Example deformable hinges may be formed from metal foils, deformable polymers, or the like.

Many conditions, e.g., herpetic ocular infections, are very difficult to treat and may require treatment with expensive and highly toxic drugs. When such drugs are applied as eye drops, many parts of the eye and areas surrounding the eye are exposed to the drugs. Such exposure may cause irritation to parts that are not targeted for treatment, e.g., tissues not affected by herpetic ocular infection. The irritation may occur in the cornea, sclera, and conjunctiva as well as the surrounding parts including the eyelids, ducts, and various glands. Indeed, due to the irritation caused by highly toxic drugs, patient compliance during treatment may be low when patients are asked to use eye drops several times a day to apply such drugs in a broad manner that irritates non-targeted tissues.

Advantageously, the drug delivery devices disclosed herein can deliver a drug focally to infected tissue while preventing any extraneous release of the drug to uninfected tissue. As described above, drug delivery devices include drug-eluting elements that can deliver a drug focally to targeted areas. The drug delivery devices also include specially configured barrier structures that minimize the amount of drug reaching uninfected tissues and unnecessary topical absorption by the uninfected tissues. In addition, as described with the delivery device 400 for instance, specially configured barrier structures can also allow irrigation of the uninfected parts of the eye without diluting the delivered drug.

The focal drug delivery devices described herein can deliver drugs to targeted tissues of the eye more effectively and may reduce treatment times. For instance, such drug delivery devices may be employed to treat conditions of the conjunctiva. In addition to herpetic ocular infections, other types of ocular conjunctival conditions include vernal conjunctivitis, allergic conjunctivitis, and giant papillary conjunctivitis. Shorter treatment times reduce the likelihood of problems that may arise during treatment of such conditions.

For instance, vernal conjunctivitis may be a significant condition for adolescents who are typically less reliable when asked to comply with conventional treatment regimes. Shorter treatment times reduce the amount of compliance required from such patients. In addition, when treating allergic conjunctivitis with antihistamines, systemic application may lead to drying effects on the cornea. Shorter treatment times may reduce the amount of drying. Furthermore, treatment of giant papillary conjunctivitis, which is associated with the overuse of contact lenses, may be complicated when patients resume use of contact lenses before the condition is fully resolved. Shorter treatment times allow patients to resume use of contact lenses more quickly, avoiding such complications.

Figure 21:
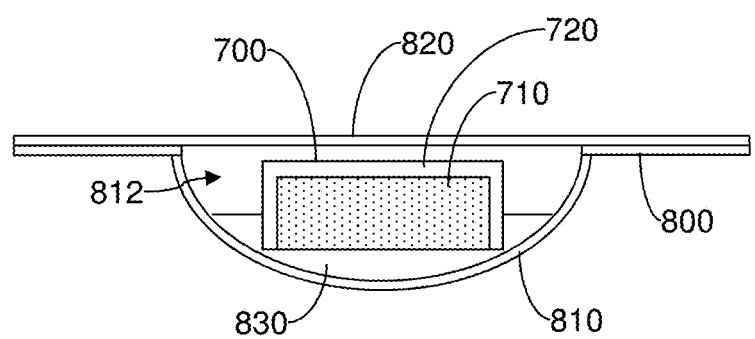
FIG. 21 illustrates an example package for a drug delivery device according to aspects of the present disclosure.

FIG. 21 illustrates an example package 800 for storing and delivering a drug delivery device 700. The package 800, for instance, may be formed as a blister pack. The package 800 includes a body 810 that may be formed (e.g., thermoformed, cold formed) from a plastic (e.g., polyvinyl chloride (PVC)) or the like. The body 810 includes a recess 812 shaped to receive the delivery device 700. The package 800 includes a removable sealing lid 820, which can be adhered to the body 810 to seal the delivery device 700 in the recess 812. The sealing lid 820 may be formed from aluminum foil, plastic, or the like.

Prior to sealing, the recess 812 can also receive a measured amount 830 of the drug to be applied by the delivery device 700. In some cases, the amount 830 may be a minimal amount constituting a single dose for the treatment. In other words, the package 800 may also be employed to store and deliver a single dose of the drug. Advantageously, the package 800 can be limited to sterile use of a single dose. In contrast, larger packages, such as syringes, ampules, or bottles, may accommodate multiple doses and allow multiple uses that increase the likelihood of compromising sterility.

In operation, the sealing lid 820 is pealed from the body 810 to unseal the recess 812. The delivery device 700 is removed from the package 800 with tweezers or other holding mechanism. As shown in FIG. 21, the delivery device 700 includes a drug-eluting element 710 and one or more barrier structures 720 similar to those described above. The barrier structures 720 may be configured to allow the delivery device 700 to be easily manipulated by the tweezers or other holding mechanism. For instance, surfaces or other aspects of the barrier structures 720 may be textured or shaped to facilitate manipulation. Additionally or alternatively, the holding mechanism may also be specially configured to facilitate manipulation.

Once the delivery device 700 is removed from the package 800, the delivery device 700 can be provided with a light shake or may be dabbed with a lint free absorbing material to allow any drug adhering to the barrier structures 720 to either wick off or be easily removed. In particular, the barrier structures 720 may be formed from a material with the appropriate hydrophilic/hydrophobic and/or lipophobic/lipophilic properties to repel the drug. Meanwhile, the drug-eluting element 710 may be formed from a material with the appropriate hydrophilic/hydrophobic and/or lipophobic/lipophilic properties to leave the drug-eluting element 710 saturated with the drug after the delivery device 700 is shaken.

In the examples above, the drug delivery devices may be applied to the targeted tissues for a length of time determined by the specific treatment regimens and the pharmacokinetics of the drug delivered to the tissue.

In some embodiments, the drug delivery device may be weighted to orient the drug delivery device when applied to the targeted tissue. For instance, the drug delivery device may achieve a particular orientation when experiencing the mechanical forces associated with blinking.

After the drug has been released to the targeted tissue and the drug delivery device is removed from the target tissue, one or more additional barrier structures may be applied to the targeted tissue to keep the drug from spreading from the targeted tissue to non-targeted tissues. These additional barriers help to maintain the advantages of the focal delivery of the drug to the targeted tissue. For instance, after the drug delivery device 600 in FIG. 20 is employed to deliver a drug to the eyelid 4, an additional barrier structure may be applied to cover the eye 1 after the delivery device 600 is removed, so that the drug does not spread from the eyelid 4 to the eye 1.

Embodiments may include additional features to enhance the treatments. For instance, in antimicrobial treatments, an antibiotic drug may be applied with a drug delivery device in combination with oxygen from an oxygen source (e.g., oxygen source 140 of the system 100). Such applications of the antibiotic drug may be more effective than merely applying the antibiotic agent in air. Indeed, lower doses of the antibiotic drug may be employed when a higher concentration of oxygen is provided.

Figure 22:
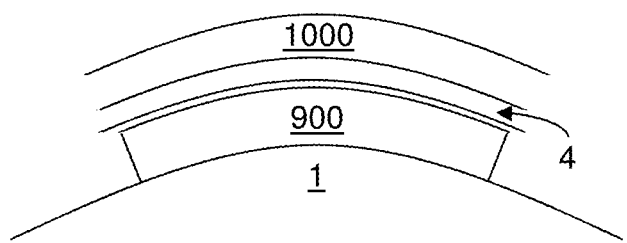
FIG. 22 illustrates an example system employing a drug delivery device according to aspects of the present disclosure.

A drug delivery device may also be employed in combination with hot compresses, gel pads, or other heating device that may be placed over the eyelids to enhance thermally the pharmacokinetics of the drug delivered focally to eye tissue. As shown in FIG. 22, a drug delivery device 900 is placed between the eye 1 and the eyelid 4. In addition, a heating device 1000 is placed on the outer surface of the eyelid 4 to enhance the treatment with the drug delivered by the delivery device 900.

As described above, according to some aspects of the present disclosure, some or all of the steps of the above-described and illustrated procedures can be automated or guided under the control of a controller (e.g., the controller 120). Generally, the controllers may be implemented as a combination of hardware and software elements. The hardware aspects may include combinations of operatively coupled hardware components including microprocessors, logical circuitry, communication/networking ports, digital filters, memory, or logical circuitry. The controller may be adapted to perform operations specified by a computer-executable code, which may be stored on a computer readable medium.

As described above, the controller may be a programmable processing device, such as an external conventional computer or an on-board field programmable gate array (FPGA) or digital signal processor (DSP), that executes software, or stored instructions. In general, physical processors and/or machines employed by embodiments of the present disclosure for any processing or evaluation may include one or more networked or non-networked general purpose computer systems, microprocessors, field programmable gate arrays (FPGA's), digital signal processors (DSP's), micro-controllers, and the like, programmed according to the teachings of the example embodiments of the present disclosure, as is appreciated by those skilled in the computer and software arts. The physical processors and/or machines may be externally networked with the image capture device(s), or may be integrated to reside within the image capture device. Appropriate software can be readily prepared by programmers of ordinary skill based on the teachings of the example embodiments, as is appreciated by those skilled in the software art. In addition, the devices and subsystems of the example embodiments can be implemented by the preparation of application-specific integrated circuits or by interconnecting an appropriate network of conventional component circuits, as is appreciated by those skilled in the electrical art(s). Thus, the example embodiments are not limited to any specific combination of hardware circuitry and/or software.

Stored on any one or on a combination of computer readable media, the example embodiments of the present disclosure may include software for controlling the devices and subsystems of the example embodiments, for driving the devices and subsystems of the example embodiments, for enabling the devices and subsystems of the example embodiments to interact with a human user, and the like. Such software can include, but is not limited to, device drivers, firmware, operating systems, development tools, applications software, and the like. Such computer readable media further can include the computer program product of an embodiment of the present disclosure for performing all or a portion (if processing is distributed) of the processing performed in implementations. Computer code devices of the example embodiments of the present disclosure can include any suitable interpretable or executable code mechanism, including but not limited to scripts, interpretable programs, dynamic link libraries (DLLs), Java classes and applets, complete executable programs, and the like. Moreover, parts of the processing of the example embodiments of the present disclosure can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the present disclosure. It is also contemplated that additional embodiments according to aspects of the present disclosure may combine any number of features from any of the embodiments described herein.

What is claimed is:

1. A drug delivery device, comprising:
   a drug-eluting element defined by a plurality of outer surfaces, the outer surfaces including a delivery surface and one or more other non-delivery surfaces, the delivery surface configured to be positioned against tissue of an eye,
   wherein the drug-eluting element is configured to release the drug to the area of targeted tissue through the delivery surface; and
   one or more barrier structures disposed along the one or more non-delivery surfaces of the drug-eluting element, the one or more barrier structures configured to substantially inhibit release of the drug from the drug-eluting element through the one or more non-delivery surfaces,
   wherein the one or more non-delivery surfaces include a first non-delivery surface opposite the delivery surface, and a second non-delivery surface extending around the drug-eluting element and between the first surface and the delivery surface,
   the one or more barriers include a first barrier disposed along the first non-delivery surface, and a second barrier disposed along the second non-delivery surface, and
   the delivery surface and the first non-delivery surface are substantially circular, the second barrier increases in thickness as it extends from the first non-delivery surface to the delivery surface, the second barrier having an outer surface that slopes radially outward with the increasing thickness, the outer surface of the side barrier configured to receive and direct lubricating or irrigating fluid to other tissue outside the targeted area of corneal tissue, the second barrier configured to substantially inhibit flow of the lubricating or irrigating fluid to the drug-eluting element and the area of targeted tissue.

2. The drug delivery device of claim 1, wherein one or more of the barrier structures are disposed around a periphery of the delivery surface and are configured to substantially inhibit flow of the drug beyond the periphery of the delivery surface.

3. The drug delivery device of claim 2, wherein the one or more barrier structures are formed from one or more materials with properties to create a surface tension with the drug that inhibits the flow beyond the periphery of the delivery surface.

4. The drug delivery device of claim 1, wherein the drug-eluting element includes pores configured to hold the drug when the delivery surface is not positioned against the tissue, and responsive to the delivery surface being positioned against the tissue, the pores are configured to release the drug into the targeted tissue according to a predetermined rate.

5. The drug delivery device of claim 1, wherein the drug-eluting element and the drug are one of hydrophilic or hydrophobic, and the one or more barrier structures are the other of hydrophilic or hydrophobic.

6. The drug delivery device of claim 1, wherein the drug-eluting element and the drug are one of lipophilic or lipophobic, and the one or more barrier structures are the other of lipophilic or lipophobic.

7. The drug delivery device of claim 1, wherein the delivery surface is textured to modify the surface of the area of the targeted tissue when the at least one delivery surface is manipulated against the targeted tissue.

8. The drug delivery device of claim 1, wherein the second barrier extends to a maximum diameter of between approximately 6 mm and approximately 11.5 mm around the delivery surface.

9. The drug delivery device of claim 1, wherein the second barrier extends to a maximum diameter of greater than approximately 11.5 mm around the delivery surface.

10. A system for drug delivery device, comprising:
a package including a recess and a removable lid sealing the recess; and
the drug delivery device of claim 1 disposed in the recess with the drug.

11. A method for drug delivery, comprising:
providing a drug delivery device, including:
a drug-eluting element defined by a plurality of outer surfaces, the outer surfaces including a delivery surface and one or more other non-delivery surfaces; and
one or more barrier structures disposed along the one or more non-delivery surfaces of the drug-eluting element;
loading the drug-eluting element with a drug;
positioning the delivery surface of the drug-eluting element against tissue of an eye; and
releasing the drug from the drug-eluting element via the delivery surface to an area of targeted tissue determined by a shape of the delivery surface,
wherein the one or more barrier structures of the drug delivery device are configured to substantially inhibit release of the drug from the drug-eluting element through the one or more non-delivery surfaces,
the one or more non-delivery surfaces include a first non-delivery surface opposite the delivery surface, and a second non-delivery surface extending around the drug-eluting element and between the first surface and the delivery surface,
the one or more barriers include a first barrier disposed along the first non-delivery surface, and a second barrier disposed along the second non-delivery surface,
the delivery device is positioned against corneal tissue, the delivery surface and the first non-delivery surface are substantially circular, the second barrier increases in thickness as it extends from the first non-delivery surface to the delivery surface, the second barrier having an outer surface that slopes radially outward with the increasing thickness, and
the method further comprises applying a lubricating or irrigating fluid to the outer surface of the side barrier to direct the lubricating or irrigating fluid to other tissue outside the targeted area of corneal tissue, the second barrier configured to substantially inhibit flow of the lubricating or irrigating fluid to the drug-eluting element and the area of targeted tissue.

12. The method of claim 11, wherein one or more of the barrier structures are disposed around a periphery of the delivery surface and are configured to substantially inhibit flow of the drug beyond the periphery of the delivery surface.

13. The method of claim 11, wherein the delivery surface is textured, and the method further comprises modifying the surface of the area of the targeted tissue by manipulating the at least one delivery surface against the targeted tissue.

14. The method of claim 11, further comprising applying a heat to the area of targeted tissue.

15. A method for drug delivery, comprising:
providing a drug delivery device, including:
a drug-eluting element defined by a plurality of outer surfaces, the outer surfaces including a delivery surface and one or more other non-delivery surfaces; and
one or more barrier structures disposed along the one or more non-delivery surfaces of the drug-eluting element;
loading the drug-eluting element with a drug;
positioning the delivery surface of the drug-eluting element against tissue of an eye; and
releasing the drug from the drug-eluting element via the delivery surface to an area of targeted tissue determined by a shape of the delivery surface,
wherein the one or more barrier structures of the drug delivery device are configured to substantially inhibit release of the drug from the drug-eluting element through the one or more non-delivery surfaces,
the one or more non-delivery surfaces include a first non-delivery surface opposite the delivery surface, and a second non-delivery surface extending around the drug-eluting element and between the first surface and the delivery surface,
the one or more barriers include a first barrier disposed along the first non-delivery surface, and a second barrier disposed along the second non-delivery surface,
the delivery device is positioned against an inner surface of an eyelid, the second barrier includes a textured scrubber surface disposed along the periphery of the delivery surface, and
the method further includes scrubbing the inner surface of the eyelid by moving the eyelid over scrubber surface.

* * * * *